(12) United States Patent
Barnes et al.

(10) Patent No.: US 8,111,162 B2
(45) Date of Patent: Feb. 7, 2012

(54) METHOD, APPARATUS AND ARTICLE FOR DETECTION OF TRANSPONDER TAGGED OBJECTS, FOR EXAMPLE DURING SURGERY

(75) Inventors: Bruce E. Barnes, Escondido, CA (US); William A. Blair, San Diego, CA (US); David A. Poirier, Escondido, CA (US)

(73) Assignee: RF Surgical Systems, Inc., Bellevue, WA (US)

( * ) Notice: Subject to any disclaimer, the term of this patent is extended or adjusted under 35 U.S.C. 154(b) by 429 days.

(21) Appl. No.: 12/473,059

(22) Filed: May 27, 2009

(65) Prior Publication Data

US 2009/0322485 A1 Dec. 31, 2009

Related U.S. Application Data

(60) Provisional application No. 61/056,787, filed on May 28, 2008, provisional application No. 61/091,667, filed on Aug. 25, 2008.

(51) Int. Cl.
 *G08B 13/14* (2006.01)
(52) U.S. Cl. ............... 340/572.1; 340/572.4; 340/539.1
(58) Field of Classification Search ............... 340/539.1, 340/539.11, 539.12, 572.1, 572.4, 635, 10.1; 128/901; 455/220, 222, 226.2, 226.3; 370/310, 370/468
See application file for complete search history.

(56) References Cited

U.S. PATENT DOCUMENTS

| 3,422,816 | A | 1/1969 | Robinson et al. ............ 128/296 |
|---|---|---|---|
| 3,587,583 | A | 6/1971 | Greenberg .................. 128/296 |
| 4,114,601 | A | 9/1978 | Abels ............................. 128/1 |
| 4,193,405 | A | 3/1980 | Abels ........................... 128/296 |
| 4,658,818 | A | 4/1987 | Miller, Jr. et al. .......... 128/303.1 |
| 4,681,111 | A | 7/1987 | Silvian ......................... 128/419 |
| 4,893,118 | A | 1/1990 | Lewiner et al. .......... 340/825.54 |
| 5,057,095 | A | 10/1991 | Fabian .......................... 604/362 |
| 5,105,829 | A | 4/1992 | Fabian et al. ................. 128/899 |
| 5,107,862 | A | 4/1992 | Fabian et al. ................. 128/899 |
| 5,188,126 | A | 2/1993 | Fabian et al. ................. 128/899 |
| 5,190,059 | A | 3/1993 | Fabian et al. ................. 128/899 |
| 5,235,326 | A | 8/1993 | Beigel et al. ............. 340/825.54 |

(Continued)

FOREIGN PATENT DOCUMENTS

WO 2004/086997 10/2004

OTHER PUBLICATIONS

International Search Report, mailed Jan. 4, 2010, for PCT/US2009/045312, 3 pages.

(Continued)

*Primary Examiner* — Van T. Trieu
(74) *Attorney, Agent, or Firm* — Seed IP Law Group PLLC

(57) ABSTRACT

The presence or absence of objects is determined by interrogating or exciting transponders coupled to the objects using pulsed wide band frequency signals. Ambient or background noise is evaluated and a threshold adjusted based on the level of noise. Adjustment may be based on multiple noise measurements or samples. Noise detection may be limited, with emphasis placed on interrogation to increase the signal to noise ratio. Match filtering may be employed. Presence/absence determination may take into account frequency and/or Q value to limit false detections. Appropriate acts may be taken if detected noise is out of defined limits of operation, for example shutting down interrogation and/or providing an appropriate indication.

37 Claims, 26 Drawing Sheets

U.S. PATENT DOCUMENTS

| | | | | |
|---|---|---|---|---|
| 5,329,944 | A | 7/1994 | Fabian et al. | 128/899 |
| 5,353,011 | A | 10/1994 | Wheeler et al. | 340/572 |
| 5,446,447 | A | 8/1995 | Carney et al. | 340/572 |
| 5,450,622 | A * | 9/1995 | Vandegraaf | 455/222 |
| 5,482,036 | A | 1/1996 | Diab et al. | 128/633 |
| 5,650,596 | A | 7/1997 | Morris et al. | 177/25.13 |
| 5,664,582 | A | 9/1997 | Szymaitis | 128/898 |
| 5,923,001 | A | 7/1999 | Morris et al. | 177/245 |
| 5,928,151 | A | 7/1999 | Hossack et al. | 600/443 |
| 6,026,818 | A | 2/2000 | Blair et al. | 128/899 |
| 6,075,797 | A * | 6/2000 | Thomas | 370/468 |
| 6,211,666 | B1 | 4/2001 | Acker | 324/207.17 |
| 6,215,437 | B1 | 4/2001 | Schürmann et al. | 342/42 |
| 6,223,137 | B1 | 4/2001 | McCay et al. | 702/184 |
| 6,270,460 | B1 | 8/2001 | McCartan et al. | 600/459 |
| 6,349,234 | B2 | 2/2002 | Pauly et al. | 607/60 |
| 6,359,562 | B2 | 3/2002 | Rubin | 340/572.3 |
| 6,366,206 | B1 | 4/2002 | Ishikawa et al. | 340/573.1 |
| 6,401,722 | B1 | 6/2002 | Krag | 128/898 |
| 6,557,752 | B1 | 5/2003 | Yacoob | 235/375 |
| 6,588,661 | B2 | 7/2003 | Degrauwe et al. | 235/382 |
| 6,632,216 | B2 | 10/2003 | Houzego et al. | 604/890.1 |
| 6,633,226 | B1 | 10/2003 | Nysen | 340/10.1 |
| 6,641,039 | B2 | 11/2003 | Southard | 235/385 |
| 6,648,223 | B2 | 11/2003 | Boukhny et al. | 235/385 |
| 6,650,240 | B2 | 11/2003 | Lee et al. | 340/572.1 |
| 6,696,954 | B2 | 2/2004 | Chung | 340/572.7 |
| 6,734,795 | B2 | 5/2004 | Price | 340/572.1 |
| 6,777,623 | B2 | 8/2004 | Ballard | 177/25.13 |
| 6,786,405 | B2 | 9/2004 | Wiedenhoefer | 235/385 |
| 6,812,842 | B2 | 11/2004 | Dimmer | 340/572.4 |
| 6,822,570 | B2 | 11/2004 | Dimmer et al. | 340/572.1 |
| 6,838,990 | B2 | 1/2005 | Dimmer | 340/572.4 |
| 6,861,954 | B2 | 3/2005 | Levin | 340/572.1 |
| 6,879,300 | B2 | 4/2005 | Rochelle et al. | 343/867 |
| 6,909,366 | B1 | 6/2005 | Marsh et al. | 340/505 |
| 6,977,504 | B2 | 12/2005 | Wright et al. | 324/326 |
| 6,998,541 | B2 | 2/2006 | Morris et al. | 177/15 |
| 7,001,366 | B2 | 2/2006 | Ballard | 604/317 |
| 7,019,650 | B2 | 3/2006 | Volpi et al. | 340/572.1 |
| 7,026,924 | B2 | 4/2006 | Gegrauwe et al. | 340/523 |
| 7,026,927 | B2 | 4/2006 | Wright et al. | 340/539.12 |
| 7,098,793 | B2 | 8/2006 | Chung | 340/572.1 |
| 7,098,866 | B2 | 8/2006 | Desjeux et al. | 343/895 |
| 7,142,815 | B2 | 11/2006 | Desjeux et al. | 455/41.2 |
| 7,158,030 | B2 | 1/2007 | Chung | 340/572.1 |
| 7,158,754 | B2 | 1/2007 | Anderson | 455/41.1 |
| 7,160,258 | B2 | 1/2007 | Imran et al. | 600/593 |
| 7,176,798 | B2 | 2/2007 | Dimmer et al. | 340/572.1 |
| 7,245,893 | B1 * | 7/2007 | Husted et al. | 455/226.3 |
| 7,256,695 | B2 | 8/2007 | Hamel et al. | 340/572.1 |
| 7,256,696 | B2 | 8/2007 | Levin | 340/572.1 |
| 7,268,684 | B2 | 9/2007 | Tethrake et al. | 340/572.1 |
| 7,299,981 | B2 | 11/2007 | Hickle et al. | 235/385 |
| 7,319,396 | B2 | 1/2008 | Homanfar et al. | 340/572.1 |
| 7,319,397 | B2 | 1/2008 | Chung et al. | 340/572.4 |
| 7,325,723 | B2 | 2/2008 | Desjeux | 235/380 |
| 7,342,497 | B2 | 3/2008 | Chung et al. | 340/572.1 |
| 7,362,228 | B2 | 4/2008 | Nycz et al. | 340/572.1 |
| 7,382,255 | B2 | 6/2008 | Chung | 340/572.1 |
| 7,397,364 | B2 | 7/2008 | Govari | 340/539.12 |
| 7,408,168 | B1 * | 8/2008 | Aufrichtig et al. | 250/370.09 |
| 7,420,468 | B2 | 9/2008 | Fabian et al. | 340/572.1 |
| 7,423,535 | B2 | 9/2008 | Chung et al. | 340/572.4 |
| 7,464,713 | B2 | 12/2008 | Fabian et al. | 128/899 |
| 7,492,257 | B2 | 2/2009 | Tethrake et al. | 340/572.1 |
| 7,508,303 | B2 | 3/2009 | Capowski et al. | 340/506 |
| 7,513,425 | B2 | 4/2009 | Chung | 235/385 |
| 2002/0032435 | A1 | 3/2002 | Levin | 606/1 |
| 2003/0004411 | A1 | 1/2003 | Govari et al. | 600/424 |
| 2003/0105394 | A1 | 6/2003 | Fabian et al. | 600/407 |
| 2004/0137844 | A1 | 7/2004 | Desjeux et al. | |
| 2004/0250819 | A1 | 12/2004 | Blair et al. | 128/899 |
| 2006/0106368 | A1 | 5/2006 | Miller et al. | 606/1 |
| 2006/0187044 | A1 | 8/2006 | Fabian et al. | |
| 2006/0202827 | A1 | 9/2006 | Volpi et al. | 340/572.1 |
| 2006/0235488 | A1 | 10/2006 | Nycz et al. | 607/60 |
| 2006/0241396 | A1 | 10/2006 | Fabian et al. | 600/424 |
| 2006/0241399 | A1 | 10/2006 | Fabian | 600/424 |
| 2007/0004994 | A1 | 1/2007 | Sherman | 602/26 |
| 2007/0005141 | A1 | 1/2007 | Sherman | 623/18.12 |
| 2007/0239289 | A1 | 10/2007 | Cambre et al. | 700/64 |
| 2007/0265690 | A1 | 11/2007 | Lichtenstein et al. | 607/116 |
| 2007/0285249 | A1 | 12/2007 | Blair et al. | 340/572.3 |
| 2008/0007411 | A1 | 1/2008 | Levin | 340/572.1 |
| 2008/0051746 | A1 | 2/2008 | Shen-Gunther | 604/362 |
| 2008/0132860 | A1 | 6/2008 | Smith et al. | 604/362 |
| 2008/0204245 | A1 | 8/2008 | Blair et al. | 340/572.1 |
| 2008/0231452 | A1 | 9/2008 | Levin | 340/572.1 |
| 2008/0237341 | A1 | 10/2008 | Fleck et al. | 235/385 |
| 2008/0238677 | A1 | 10/2008 | Blair et al. | 340/572.1 |
| 2008/0272913 | A1 | 11/2008 | Barnes et al. | 340/572.1 |
| 2008/0281190 | A1 | 11/2008 | Petcavich et al. | 600/424 |
| 2008/0296373 | A1 | 12/2008 | Zmood et al. | 235/385 |

OTHER PUBLICATIONS

Written Opinion, mailed Jan. 4, 2010, for PCT/US2009/045312, 3 pages.
U.S. Appl. No. 12/472,199, filed May 26, 2009, Blair.
U.S. Appl. No. 61/109,104, filed Oct. 28, 2008, Blair et al.
U.S. Appl. No. 61/222,443, filed Jul. 1, 2009, Blair et al.
U.S. Appl. No. 61/222,847, filed Jul. 2, 2009, Blair et al.
Macario, A. et al, "Initial Clinical Evaluation of a Handheld Device for Detecting Retained Surgical Gauze Sponges Using Radiofrequency Identification Technology," *Arch. Surg. 141*:659-662, Jul. 2006.

* cited by examiner

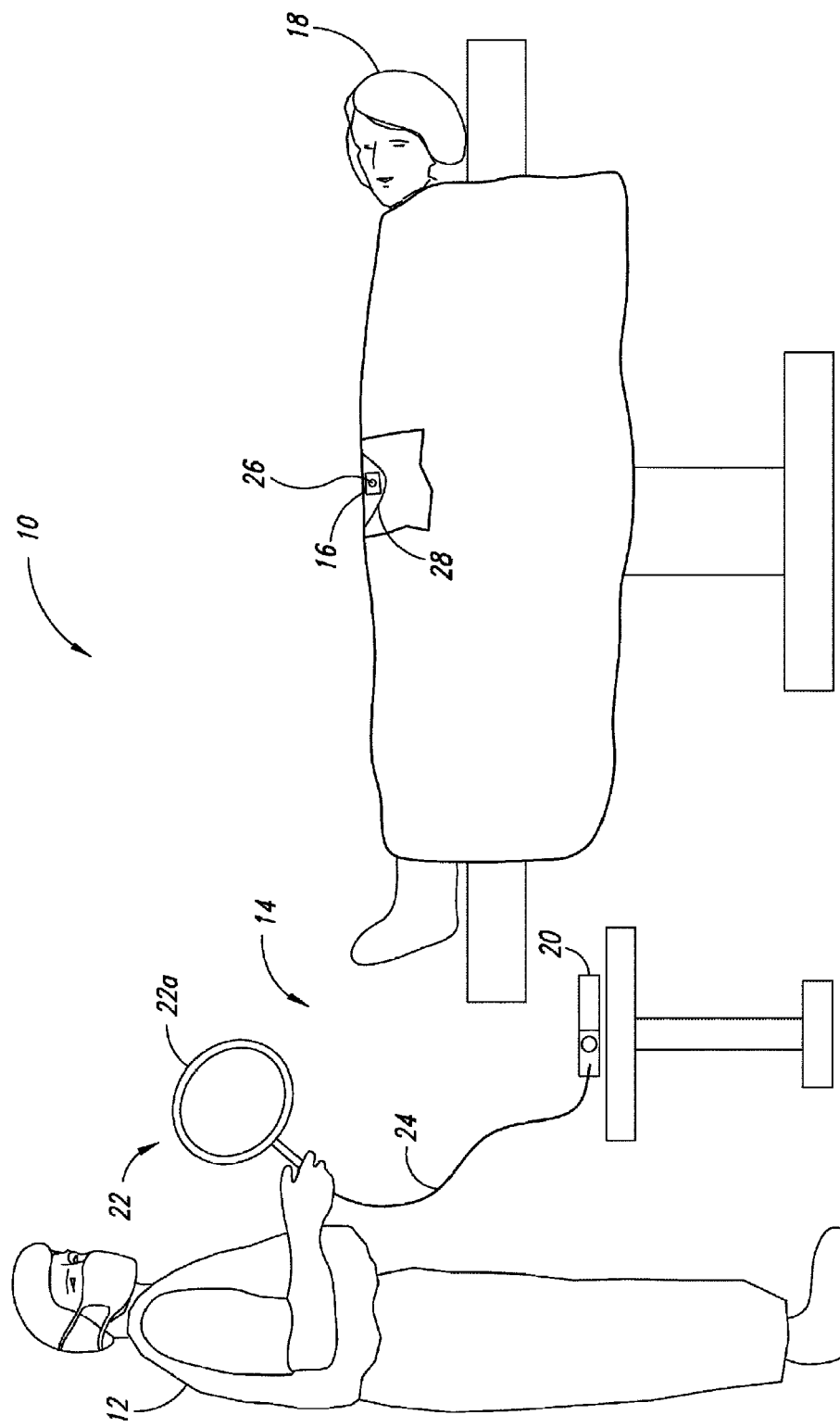

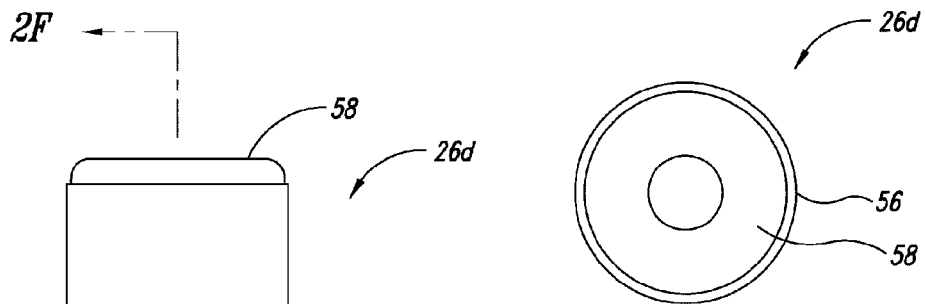
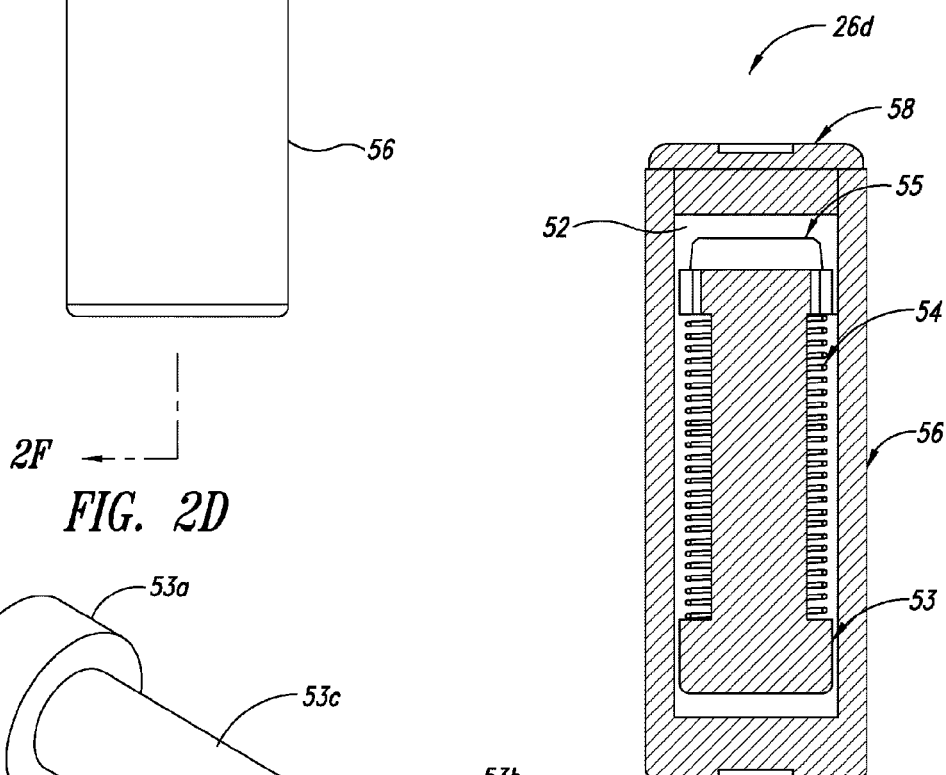
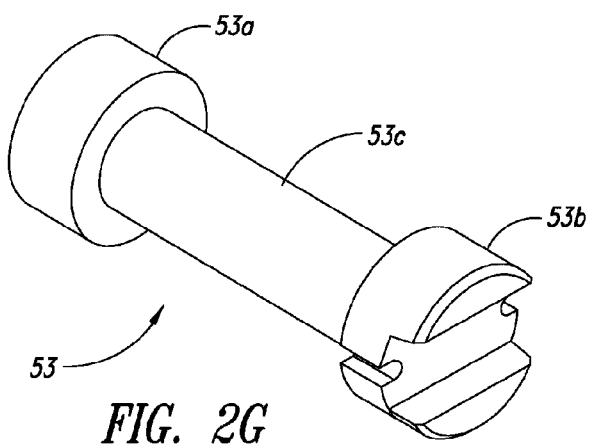
FIG. 2D
FIG. 2E
FIG. 2F
FIG. 2G

```
                                                    ┌─2100
┌─────────────────────────────────────────────────────┐
│ ADJUST SIGNAL DETECTION THRESHOLD BASED AT LEAST IN PART ON │
│ DETERMINED NOISE VALUES FOR NOISE DETECTION PORTIONS THAT   │─2102
│ OCCURRED BEFORE AND AFTER RECEIVE RESPONSE PORTION          │
└─────────────────────────────────────────────────────┘
```

FIG. 21

```
                                                    ┌─2200
┌─────────────────────────────────────────────────────┐
│ ADJUST SIGNAL DETECTION THRESHOLD TO APPROXIMATELY TWICE    │
│ AVERAGE OF DETERMINED NOISE VALUES THAT OCCURRED BEFORE AND │─2202
│ AFTER RECEIVE RESPONSE PORTION                              │
└─────────────────────────────────────────────────────┘
```

FIG. 22

```
                                                    ┌─2300
┌─────────────────────────────────────────────────────┐
│ ADJUST SIGNAL DETECTION THRESHOLD TO APPROXIMATELY TWICE    │
│ GREATEST OF AT LEAST ONE OF THE DETERMINED NOISE VALUES THAT│─2302
│ OCCURRED BEFORE AND AFTER RECEIVE RESPONSE PORTION          │
└─────────────────────────────────────────────────────┘
```

FIG. 23

```
                                                    ┌─2400
┌─────────────────────────────────────────────────────┐
│ COMPARE MAXIMUM VALUE OF MATCHED FILTER OUTPUTS WITH        │─2402
│ ADJUSTED SIGNAL THRESHOLD                                   │
└─────────────────────────────────────────────────────┘
```

FIG. 24

```
                                                    ┌─2500
┌─────────────────────────────────────────────────────┐
│ ADJUST SIGNAL DETECTION THRESHOLD TO LARGER OF APPROXIMATELY│─2502
│ TWICE DETERMINED NOISE VALUE                                │
└─────────────────────────────────────────────────────┘
```

FIG. 25

METHOD, APPARATUS AND ARTICLE FOR DETECTION OF TRANSPONDER TAGGED OBJECTS, FOR EXAMPLE DURING SURGERY

CROSS-REFERENCE(S) TO RELATED APPLICATION(S)

This application claims the benefit under 35 U.S.C. §119 (e) of U.S. Provisional patent application Ser. No. 61/056,787, filed May 28, 2008 and U.S. Provisional patent application Ser. No. 61/091,667, filed Aug. 25, 2008.

BACKGROUND

1. Field

This disclosure generally relates to the detection of the presence or absence of objects tagged with transponders, which may, for example, allow the detection of surgical objects during surgery.

2. Description of the Related Art

It is often useful or important to be able to determine the presence or absence of an object.

For example, it is important to determine whether objects associated with surgery are present in a patient's body before completion of the surgery. Such objects may take a variety of forms. For example, the objects may take the form of instruments, for instance scalpels, scissors, forceps, hemostats, and/or clamps. Also for example, the objects may take the form of related accessories and/or disposable objects, for instance surgical sponges, gauzes, and/or pads. Failure to locate an object before closing the patient may require additional surgery, and in some instances may have serious adverse medical consequences.

Some hospitals have instituted procedures which include checklists or requiring multiple counts to be performed to track the use and return of objects during surgery. Such a manual approach is inefficient, requiring the time of highly trained personnel, and is prone to error.

Another approach employs transponders and a wireless interrogation and detection system. Such an approach employs wireless transponders which are attached to various objects used during surgery. The interrogation and detection system includes a transmitter that emits pulsed wideband wireless signals (e.g., radio or microwave frequency) and a detector for detecting wireless signals returned by the transponders in response to the emitted pulsed wideband signals. Such an automated system may advantageously increase accuracy while reducing the amount of time required of highly trained and highly compensated personnel. Examples of such an approach are discussed in U.S. Pat. No. 6,026,818, issued Feb. 22, 2000, and U.S. patent Publication No. US 2004/0250819, published Dec. 16, 2004.

Commercial implementation of such an automated system requires that the overall system be cost competitive and highly accurate. In particular, false negatives must be avoided to ensure that objects are not mistakenly left in the patient. Some facilities may wish to install a single interrogation and detection system in each surgery theater, while other facilities may move an interrogation and detection system between multiple surgical theaters. In either case, the overall system will require a large number of transponders, since at least one transponder is carried, attached or otherwise coupled to each object which may or will be used in surgery. Consequently, the transponders must be inexpensive. However, inexpensive transponders typically have a relatively large variation in the frequency of signals they emit, making it difficult to accurately detect the signals returned by the transponders. This may be particularly difficult in some environments which are noisy with respect to the particular resonant frequencies of the transponders. Consequently, a new approach to detection of the presence and absence of transponder that facilitates the use of inexpensive transponders is highly desirable.

BRIEF SUMMARY

At least one embodiment may be summarized as a method of operation of a transponder detection device, including, during each of a plurality of detection cycles, receiving electromagnetic signals during a noise detection portion of the detection cycle; determining a noise value indicative of a noise level that corresponds to a highest one of a number N of samples or measurements of the electromagnetic signals received during the noise detection portion of the detection cycle, where the number N is greater than one; adjusting a signal detection threshold based at least in part on the determined noise value of at least one of the detection cycles; emitting at least one electromagnetic interrogation signal during a transmit portion of the detection cycle; receiving electromagnetic signals during a receive response portion of the detection cycle that follows the transmit portion of the detection cycle; and determining the presence or absence of a transponder based at least in part on a number M of samples or measurements of the electromagnetic signals received during the detection cycle and the adjusted signal detection threshold, where the number M is greater than one. The received signals may be unmodulated electromagnetic signals.

The method may further include determining a noise value indicative of a noise level based at least in part on the electromagnetic signals received during the noise detection portion of the detection cycle including setting the noise value based on the highest one of six samples or measurements of the electromagnetic signal received during the noise detection portion of the detection cycle. The method may further include adjusting a signal detection threshold based at least in part on the determined noise value of at least one of the detection cycles including adjusting the signal detection threshold based at least in part on a first number of determined noise values indicative of a noise level during at least one noise detection portion that occurred before the receive response portion of a first one of the detection cycles and a second number of determined noise values indicative of a noise level during at least one noise detection portion that occurred after the receive response portion of the first one of the detection cycles. The method may further include adjusting a signal detection threshold based at least in part on the determined noise value of at least one of the detection cycles including adjusting the signal detection threshold to be approximately twice an average of at least one of the first and the second number of determined noise values. The method may further include adjusting a signal detection threshold based at least in part on the determined noise value of at least one of the detection cycles including adjusting the signal detection threshold to be approximately twice a greatest one of at least one of the first and the second number of determined noise values. The method may further include determining the presence or absence of a transponder including comparing a maximum value of a plurality of matched filter outputs with the adjusted signal threshold. The method may further include adjusting a signal detection threshold based at least in part on the determined noise value of at least one of the detection cycles including adjusting the signal detection threshold to be approximately twice the determined noise value. The method may further include adjusting a signal detection threshold based at least in part on the determined noise value of at least one of the detection cycles including adjusting the signal detection threshold to be the large of approximately twice the determined noise value or a defined threshold value. The method may further include the defined threshold value being approximately 0.5 mV. The method may further include a ratio of N:M being at least equal to 4. The method may further include N being equal to about 200 and M being equal to about 800. The method may further include determining if an output of at least one matched filter during the noise detection portion of the detection cycle exceeds a noise fault threshold indicative of a noise fault. The method may further include determining if the output of the at least one matched filter during the noise detection portion of the detection cycle exceeds the noise fault threshold for a defined period of time; and terminating the detection cycle in response to the output of the at least one matched filter exceeding the noise fault threshold for the defined period of time. The method may further include emitting at least one electromagnetic interrogation signal during a transmit portion of the detection cycle including emitting at least one electromagnetic interrogation signal in each of a 136 KHz band, a 139 KHz band, a 142 KHz band, a 145 KHz band, a 148 KHz band, a 151 KHz band and a 154 KHz band. The method may further include ignoring any electromagnetic signals received during a recovery portion of the detection cycle that precedes the receive response portion of the detection cycle. The method may further include dumping energy from an antenna circuit during a dump portion of the detection cycle that precedes the recovery portion of the detection cycle. The method may further include, for each successive pair of detection cycles, varying a time between a start of a first one of the successive pairs of the detection cycles and a start of a next successive one of the pairs of the detection cycles. The method may further include the transmit and the receive response portions each occurring during an interrogation portion of the detection cycle, which follows the noise detection portion of the detection cycle. The method may further include emitting at least one electromagnetic interrogation signal during a transmit portion of the detection cycle including emitting a first wide band electromagnetic interrogation signal during a first transmit portion of the detection cycle and emitting at least a second wide band electromagnetic interrogation signal during a second transmit portion of the detection cycle. Determining the presence or absence of a transponder may be based at least in part on a frequency of the electromagnetic signals received during the detection cycle being within a defined frequency range. The defined frequency range may extend from about 137 KHz to about 160 KHz. Determining the presence or absence of a transponder may be based at least in part on a Q value of the electromagnetic signals received during the detection cycle. Determining the presence or absence of a transponder may be based at least in part on a Q value of the electromagnetic signals received during the detection cycle being at least equal to a threshold Q value. The threshold Q value may be 35.

At least one embodiment may be summarized as a transponder detection system, including a transmitter to transmit electromagnetic interrogation signals during at least one transmit portion of each of a plurality of detection cycles; a receiver to receive electromagnetic signals during a noise detection portion and during a receive response portion of each of the detection cycles; a noise level determiner that determines a noise level that corresponds to a highest one of a number N of samples or measurements of the electromagnetic signals received during the noise detection portion of the detection cycles, the noise detection portion temporally spaced from the transmit portions such that transponders are not responding to the electromagnetic interrogation signals; a detection threshold adjuster to adjust a detection threshold of the transponder detection system based at least in part on at least one value indicative of at least one of the noise levels; and a presence or absence determiner to determine the presence or absence of the transponders based at least in part on a number M of samples or measurements of the received electromagnetic signals and the adjusted detection threshold. The received signals may be unmodulated electromagnetic signals.

The noise level determiner may be configured to set the noise value based on the highest one of six samples or measurements of the electromagnetic signal received during the noise detection portion of the detection cycle. The detection threshold adjuster may be configured to adjust the signal detection threshold based at least in part on a first number of determined noise values indicative of a noise level during at least one noise detection portion that occurred before the receive response portion of a first one of the detection cycles and a second number of determined noise values indicative of a noise level during at least one noise detection portion that occurred after the receive response portion of the first one of the detection cycles. The transponder detection system may include a comparator coupled to determine if the output of the at least one matched filter during the noise detection portion of the detection cycle exceeds the noise fault threshold for a defined period of time; and wherein the controller is configured to terminate the detection cycle in response to the output of the at least one matched filter exceeding the noise fault threshold for the defined period of time. The controller may be configured to ignore any electromagnetic signals received during a recovery portion of the detection cycle that precedes the receive response portion of the detection cycle; to dump energy from an antenna circuit during a dump portion of the detection cycle that precedes the recovery portion of the detection cycle; and to vary a time between a start of a first one of the successive pairs of the detection cycles and a start of a next successive one of the pairs of the detection cycles. The transmitter may include a frequency adjuster configured to adjust a center frequency of the electromagnetic interrogation signals between successive transmit portions of the detection cycle. The presence or absence determiner may determine presence or absence be based at least in part on a frequency of the electromagnetic signals received during the detection cycle being within a defined frequency range. The defined frequency range may extend from about 137 KHz to about 160 KHz. The presence or absence determiner may determine presence or absence based at least in part on a Q value of the electromagnetic signals received during the detection cycle. The presence or absence determiner may determine the presence or absence of a transponder based at least in part on a Q value of the electromagnetic signals received during the detection cycle being at least equal to a threshold Q value. The threshold Q value may be 35.

BRIEF DESCRIPTION OF THE SEVERAL VIEWS OF THE DRAWING(S)

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 1 is a schematic diagram showing a surgical environment illustrating a medical provider using an interrogation and detection system to detect an object tagged with a transponder in a patient, according to one illustrated embodiment.

FIG. 2D is a side elevational view of a transponder, according to yet a further illustrated embodiment.

FIG. 2E is an end view of the transponder of FIG. 2D.

FIG. 2F is a cross-sectional view of the transponder of FIG. 2D, taken along section line 2F.

FIG. 2G is an isometric view of a ferrite core of the transponder of FIG. 2D.

Figure 19:
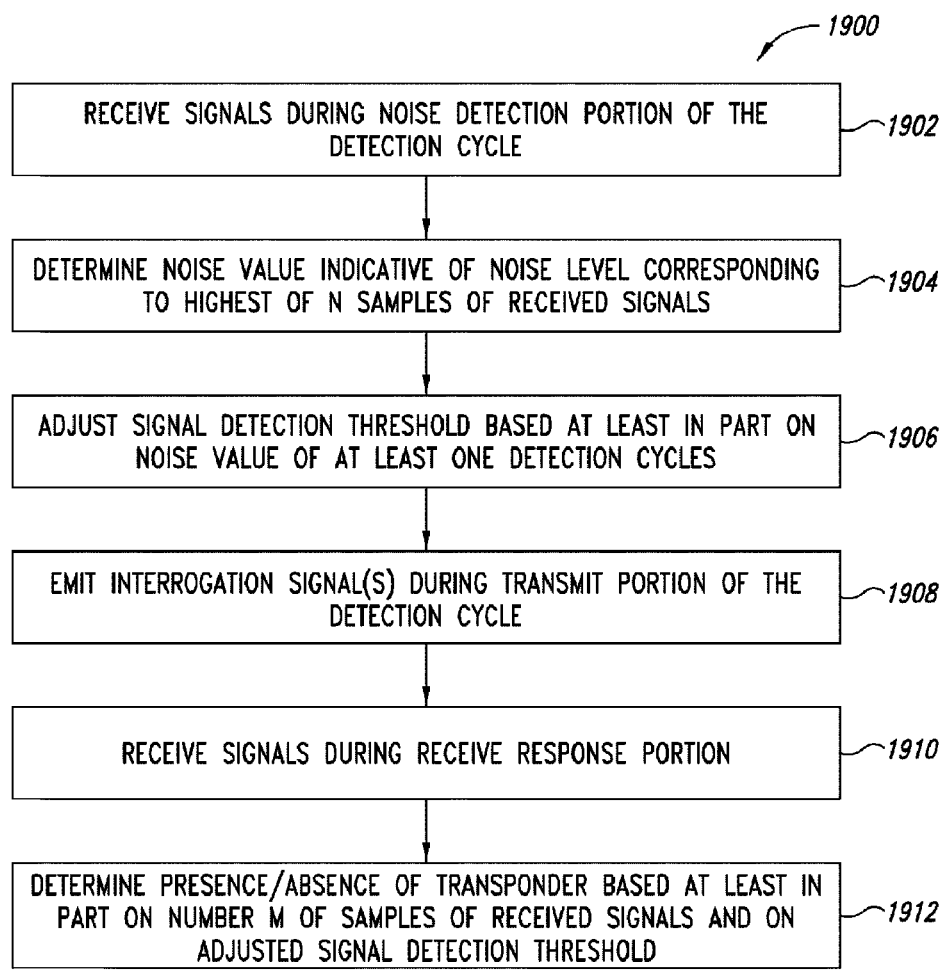

FIG. 19 is a flow diagram showing a method of operating an interrogation and detection system according to one illustrated embodiment, including receiving electromagnetic signals, for example unmodulated electromagnetic signals, determining a noise value, adjusting signal detection threshold, emitting interrogations signals, receiving electromagnetic signals, and determining a presence or absence of a transponder based at least in part on the adjusted signal detection threshold.

Figure 20:
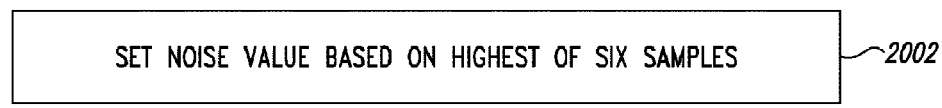

FIG. 20 is a flow diagram showing a method of determining a noise value in an interrogation and detection system, according to one illustrated embodiment.

FIG. 21 is a flow diagram showing a method of adjusting the signal detection threshold in an interrogation and detection system including, according to one illustrated embodiment.

FIG. 22 is a flow diagram showing a method of adjusting the signal detection threshold in an interrogation and detection system, according to one illustrated embodiment.

FIG. 23 is a flow diagram showing a method of adjusting the signal detection threshold in an interrogation and detection system, according to one illustrated embodiment.

FIG. 24 is a flow diagram showing a method of determining the presence or absence of a transponder in an interrogation and detection system, according to one illustrated embodiment.

FIG. 25 is a flow diagram showing a method of adjusting the signal detection threshold in an interrogation and detection system, according to one illustrated embodiment.

Figure 26:
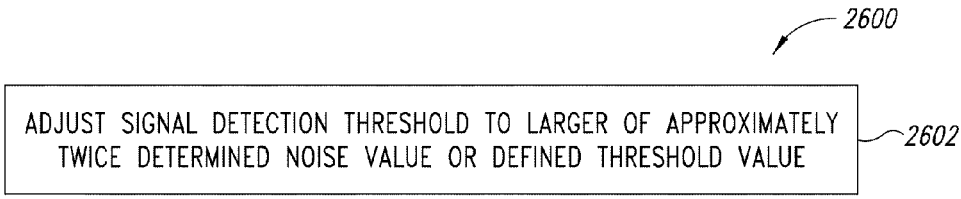

FIG. 26 is a flow diagram showing a method of adjusting the signal detection threshold in an interrogation and detection system, according to one illustrated embodiment.

Figure 27:
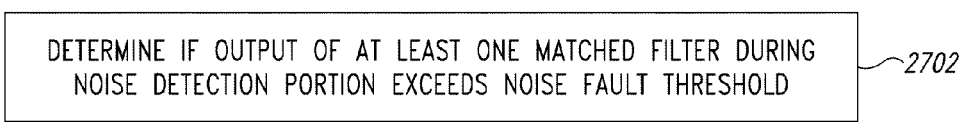

FIG. 27 is a flow diagram showing a method of determining an occurrence of a noise fault in an interrogation and detection system, according to one illustrated embodiment.

Figure 28:
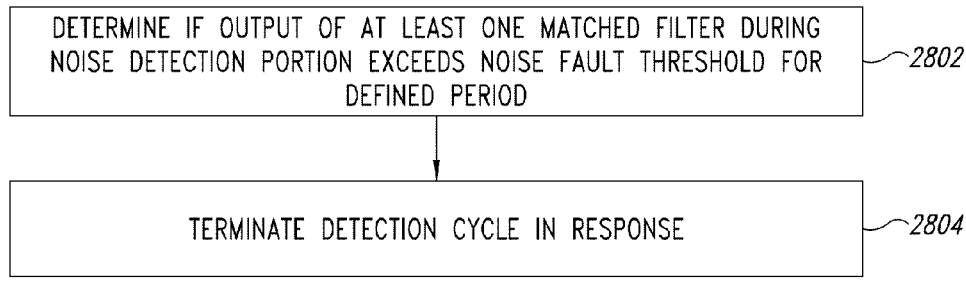

FIG. 28 is a flow diagram showing a method of determining an occurrence of a noise fault in an interrogation and detection system, according to another illustrated embodiment.

Figure 29:
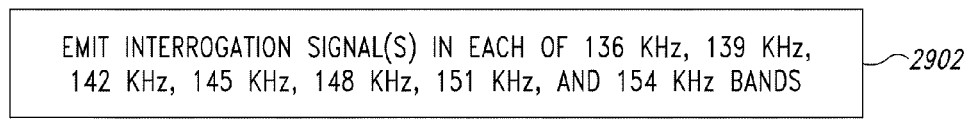

FIG. 29 is a flow diagram showing a method of emitting electromagnetic interrogation signal(s) in an interrogation and detection system, according to one illustrated embodiment.

Figure 30:
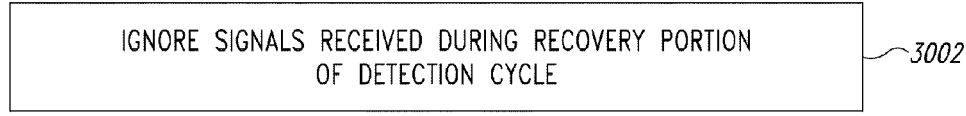

FIG. 30 is a flow diagram showing a method of eliminating false positives in an interrogation and detection system, according to one illustrated embodiment.

Figure 31:
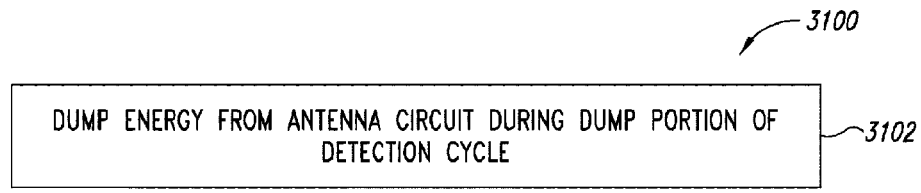

FIG. 31 is a flow diagram showing a method of eliminating false positives in an interrogation and detection system, according to another illustrated embodiment.

Figure 32:
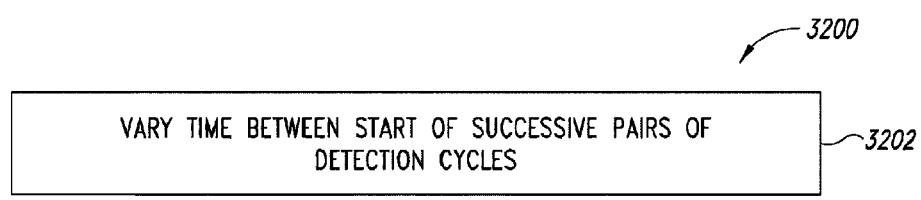

FIG. 32 is a flow diagram showing a method of de-correlating response signals in an interrogation and detection system, according to one illustrated embodiment.

Figure 33:
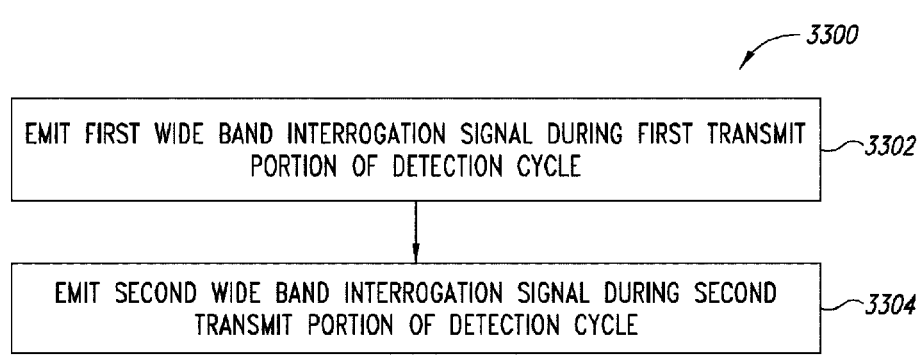

FIG. 33 is a flow diagram showing a method of emitting electromagnetic interrogation signal(s) in an interrogation and detection system, according to one illustrated embodiment.

Figure 34:
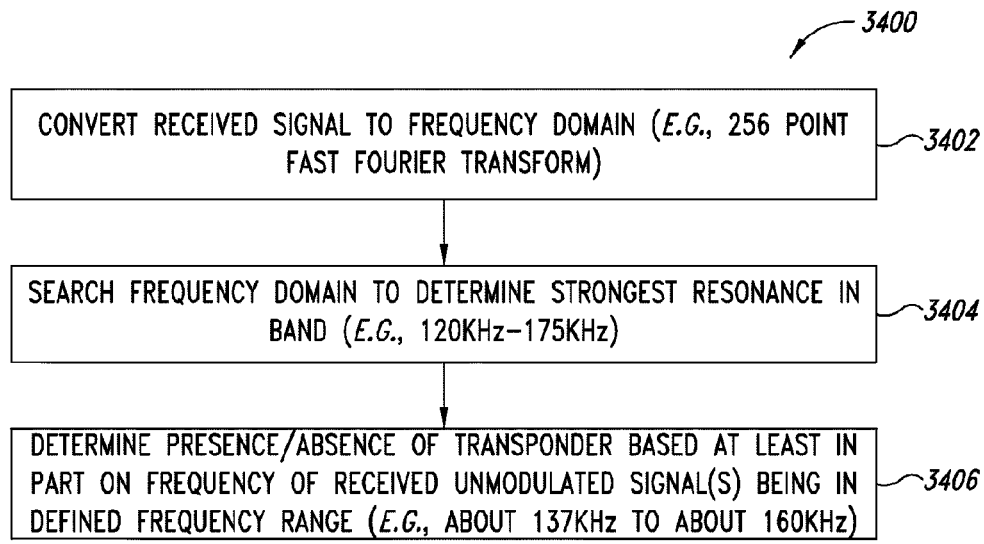

FIG. 34 is a flow diagram showing a method of determining the presence or absence of a transponder employing a frequency domain spectrum in an interrogation and detection system, according to one illustrated embodiment.

Figure 35:
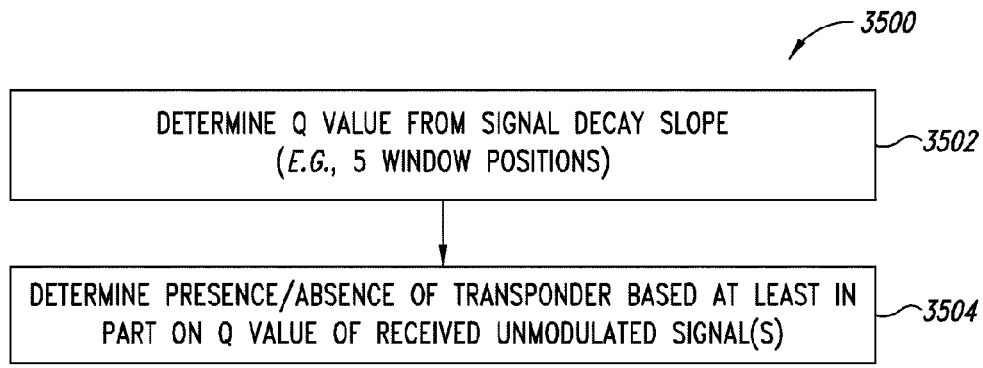

FIG. 35 is a flow diagram showing a method of determining the presence or absence of a transponder employing a Q value in an interrogation and detection system, according to one illustrated embodiment.

Figure 36:
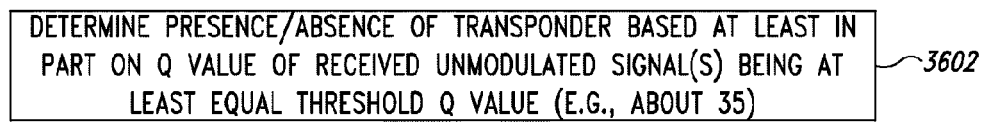

FIG. 36 is a flow diagram showing a method of determining the presence or absence of a transponder employing a Q value in an interrogation and detection system, according to another illustrated embodiment.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

FIG. 1 shows a surgical environment 10 in which a medical provider 12 operates an interrogation and detection system 14 to ascertain the presence or absence of objects 16 in, or on, a patient 18. The interrogation and detection system 14 may include a controller 20, and an antenna 22 coupled to the controller 20 by one or more communication paths, for example coaxial cable 24. The antenna 22 may take the form of a hand-held wand 22a.

The object 16 may take a variety of forms, for example instruments, accessories and/or disposable objects useful in performing surgical procedures. For instance, the object 16 may take the form of scalpels, scissors, forceps, hemostats, and/or clamps. Also for example, the objects 16 may take the form of surgical sponges, gauze and/or padding. The object 16 is tagged, carrying, attached or otherwise coupled to a transponder 26. Embodiments of the interrogation and detection system 14 disclosed herein are particularly suited to operate with transponders 26 which are not accurately tuned to a chosen or selected resonant frequency. Consequently, the transponders 26 due not require high manufacturing tolerances or expensive materials, and thus may be inexpensive to manufacture.

In use, the medical provider 12 may position the wand 22a proximate the patient 18 in order to detect the presence or absence of the transponder 26. and hence an object 16 The medical provider 12 may in some embodiments move the wand 22a along and/or across the body of the patient 18. In some embodiments, the wand 22a may be sized to fit at least partially in a body cavity 28 of the patient 18.

Figure 2A:
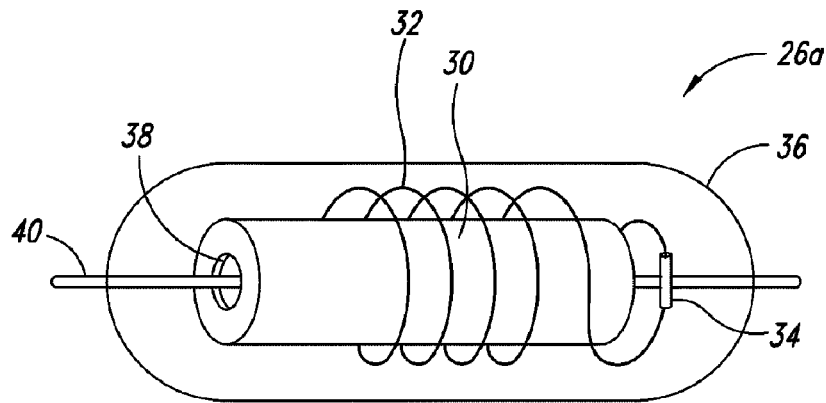
FIG. 2A is a schematic diagram of a transponder, according to one illustrated embodiment.

FIG. 2A shows a transponder 26a according to one illustrated embodiment.

The transponder 26a includes a miniature ferrite rod 30 with a conductive coil 32 wrapped about an exterior surface thereof to form an inductor (L), and a capacitor (C) 34 coupled to the conductive coil 32 to form a series LC circuit. The conductive coil 32 may, for example, take the form of a spiral wound conductive wire with an electrically insulative sheath or sleeve. The transponder 26a may include an encapsulation 36 that encapsulates the ferrite rod 30, conductive coil 32, and capacitor 34. The encapsulant 36 may be a bio-inert plastic, that protects the ferrite rod 30, conductive coil 32 and/or capacitor 34 from pressure and/or from fluids, for example bodily fluids.

In some embodiments, the ferrite rod 30 may include a passage 38 sized to receive a physical coupler, for example a bonding tie or string 40. The bonding tie or string 40 may take the form of an elastomeric x-ray opaque flexible elongated member, that may be used to attach the transponder 26a to various types of objects 16, for example surgical sponges. The transponder 26a may have a length of about 8 millimeters and a diameter of about 2 millimeters. Employing such small dimensions ensures that the transponder 26a does not impede deformation of objects 16 such as sponges. The transponder 26a may include an optional diode (not shown), to protect against over-voltage occurrences caused by other electronic instruments.

Figure 2B:
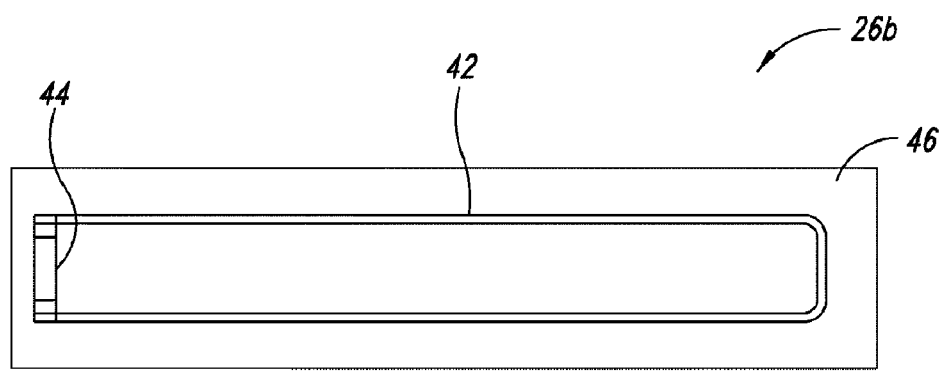
FIG. 2B is a schematic diagram of a transponder, according to another illustrated embodiment.

FIG. 2B shows a transponder 26b, according to another illustrated embodiment.

The transponder 26b includes a single loop of conductive material 42, for example a loop of conductive wire forming an inductor (L), coupled in series to a capacitor 44 (C) to form an LC series circuit. The loop of conductive material 42 and capacitor 44 may be encapsulated in an elastomeric coating or sleeve 46. The dimensions of the transponder 26b may be similar to the dimensions of the transponder 26a. In some embodiments, the dimensions of the transponder 26b are greater than the dimensions of the transponder 26a. The transponder 26b is highly flexible, and thus may provide its own thread-like or string-like attachment to various types of objects 16.

Figure 2C:
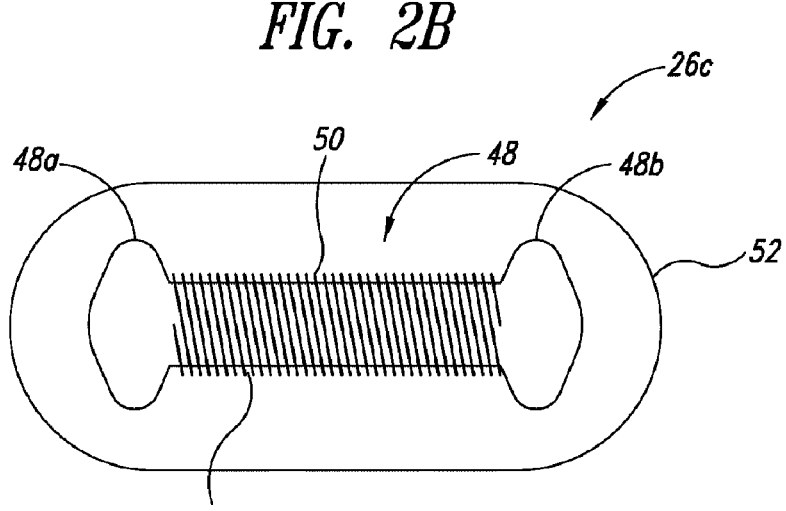
FIG. 2C is a schematic diagram of a transponder, according to a further illustrated embodiment.

FIG. 2C shows a transponder 26c according to a further embodiment.

The transponder 26c includes a dumbbell-shaped ferrite rod 48 having broad end portions 48a, 48b, and a narrow intermediate portion 48c which is wrapped by a conductive coil 50. The broad portions 48a, 48b contain the conductive coils 50. Such a design may provide stronger and/or more reliable signal emission than transponders 26a, 26b fashioned with cylindrical ferrite rods. The transponder 26c may optionally include an encapsulant 52. Further details regarding the transponder 26c may be found in U.S. Provisional patent application No. 60/811,376 filed Jun. 6, 2006. In some embodiments, the transponder 26c may be formed as a fusiform-shaped object, with truncated ends. The fusiform shape may be advantageous over cylindrical shaped transponders 26a, 26b in reducing the likelihood of close parallel alignment of the transponders 26a, 26b, which may produce transponder-to-transponder interaction and interference.

FIGS. 2D-2G show a transponder 26d according to yet a further embodiment.

The transponder 26d includes a ferrite core 53, inductor (L) 54, and capacitor© 55 electrically coupled to the inductor 54 to form an LC series circuit. The transponder 26d also includes a capsule 56 with a cavity 57 open at one end to receive the ferrite core 53, inductor 54 and capacitor 55, as well as a lid 58 to close the open end of the capsule 56.

The ferrite core 53 may, for example, take the form of a soft ferrite drum, and may, for example, be formed of Nickel Zinc. Suitable ferrite cores 53 may be commercially available from TAK FERRITE as part no. L8A DR3X9 B=1.8 F=6 or from HUAHYOW under part no. 10R030090-77S. The drum may have a pair of larger diameter end portions 53a, 53b, with a smaller diameter intermediate portion 53c therebetween.

The inductor 54 may take the form of magnet wire wrapped around the intermediate portion 53c of the ferrite core 53. The magnet wire may, for example, have a dimension of approximately 41 American Wire Gauge (AWG), although some embodiments may employ wires or conductors of larger or small gauges. Suitable inductors 54 may be commercially available from ELEKTISOLA under part no. PN-155 or from ROSEN under part no. 2UEW-F. The inductor may, for example, include approximately 432 turns, over approximately 6.5 layers, although some embodiments may include a greater or lesser number of turns and/or layers. The transponder 26d may include tape and/or epoxy enveloping the inductor 54. Suitable tape may be commercially available from 3M under part nos. 1298, 1350-1 or PLEO1P801, while suitable epoxy may be commercially available from LOCKTITE under part no. 3211.

The capacitor 55 may, for example, take the form of a ceramic capacitor. The capacitor 55 may, for example, have a capacitance of 470 PF, 100V, with a Quality factor of Q>2200@1 MHz. Suitable capacitors 55 may be commercially available from SANJV DIELECTRIC under part no. 0805NPO471J101 or from FENG HUA under part no. 0805CG471J101 NT.

The capsule 56 and lid 58 may, for example, be formed of a polypropylene. Suitable capsules 56 and lids 58 may be commercially available from WEITHE ELECTRON (HK) COMPANY, under part specification CASE 4.3×12.6. The combination of the capsule 56 and lid 58 may, for example, have a length of approximately 12.8 mm and a diameter of 4.4 mm. Circuit bonds may, for example, employ UNITED RESINS CORP. part no. 63001500 CIRCUIT BOND LV, while solder may take the form of a lead free 96.5% Ag/3% Sn/0.5 Cu solder.

The transponders 26 may be attached to hemostats, scissors, certain forms of forceps, and the like. In some embodiments, the transponders 26 may be coupled to the object 16 by way of a clamp or holder. In some embodiments, the transponders 26 may be retained within a cavity of the holder. In some embodiments, the holder may be fashioned of a durable deformable material, such as surgical grade polymer, which may be deformed to clamp securely onto the finger or thumbhole of an instrument. In other embodiments, the transponders 26 may be attached to objects 16 by way of pouches fashioned of sheet material (e.g., surgical fabric) surrounding the transponder 26. The transponder 26 is retained within the pouch, and in some embodiments the pouch may be sewn or otherwise sealed. Sealing may be done with adhesive, hot glue, clamping, grommeting, or the like.

Figure 3A:
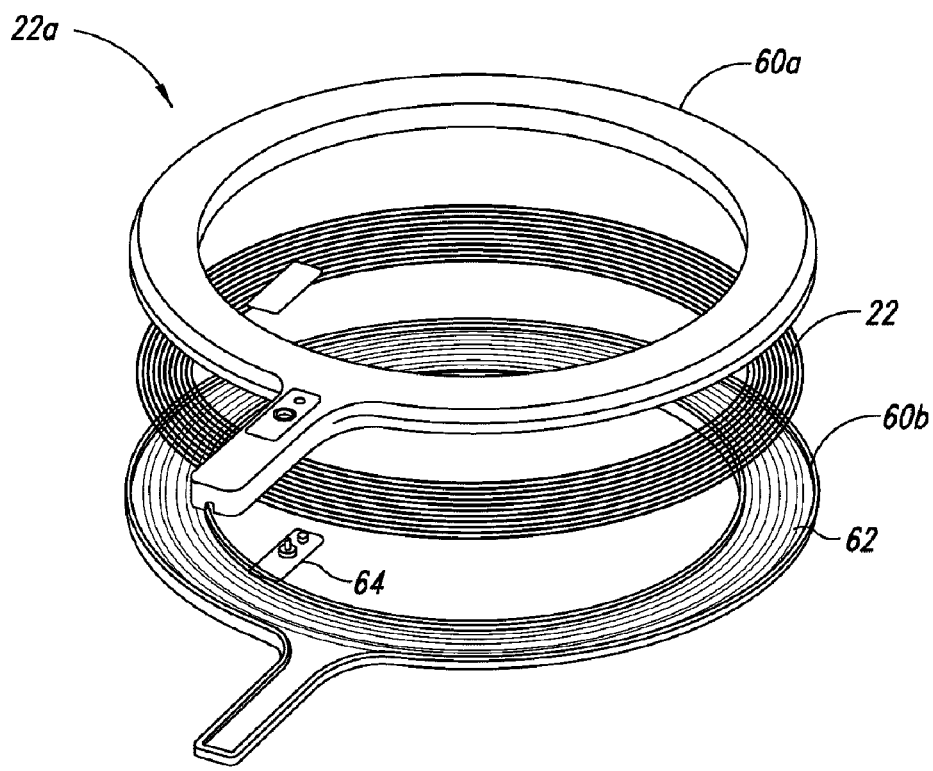
FIG. 3A is an exploded view of a wand of the interrogation and detection system, according to one illustrated embodiment.
Figure 3B:
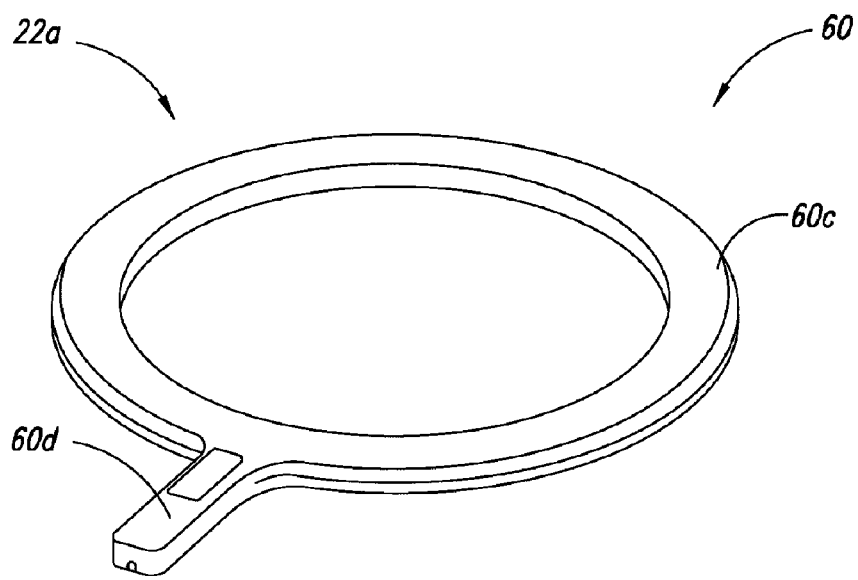
FIG. 3B is an isometric view of the wand of FIG. 3A.

FIGS. 3A and 3B show a wand 22a, according to one illustrated embodiment.

The wand 22a may include a first housing structure 60a and a second housing structure 60b which mates to the first housing structure 60a to form a housing 60. The housing 60 may include an annular portion 60c and a handle portion 60d extending from the annular portion. The handle portion may be sized and dimensioned to be gripped by the hand of a medical provider 12 (FIG. 1). In some embodiments, the housing portions 60a, 60b may be identical in shape to one another.

The housing 60 may define one or more cavities 62 sized and dimensioned to receive the antenna 22. The antenna 22 may, for example, take the form of an annulus or air-coil formed of coils of conductive material, for example wire. In one embodiment, the antenna 22 includes 10 turns evenly spaced between an inner diameter of about 11 inches and an outer diameter of about 14 inches. The antenna 22 acts as an inductor.

The wand 22a may include a coupling member 64 which may be positioned in the cavity in the handle portion 60d to provide a connector to communicatively couple to an end of the coaxial cable 24 to the antenna 22. The coupling member 64 may take the form of a standard coaxial connector. Some embodiments may employ other types of communications pathways between the controller 20 and the antenna 22, and thus may employ other types of coupling members or connectors.

In some embodiments, the wand 22a may include one or more user interface devices, for example one or more visual indicators to provide visual indications to the medical provider 12. Such may, for example, take the form of one or more light emitting diodes, which may produce one or more different colors. Such user interface devices may additionally, or alternatively include a speaker or other transducer, operable to produce a sound or other sensory indication, for example a tactile sensation. Such user interface devices may be configured to provide sensory feedback to the medical provider 12 indicative of an operating condition of the interrogation and detection system 14. For example, such may indicate when the interrogation and detection system 14 is operating, when the presence of a transponder 26 has been identified, and/or when an error has occurred. Locating user interface devices on the wand 22a may be advantageous since the medical provider 12 will typically focus their attention on the wand 22a while scanning the patient 18.

Figure 4:
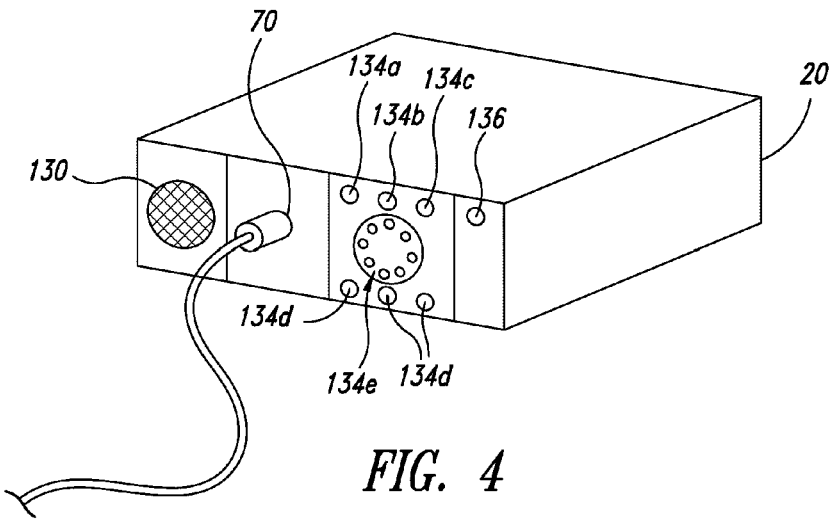
FIG. 4 is an isometric view of a controller of the interrogation and detection system, according to one illustrated embodiment.

FIG. 4 shows the controller 20 according to one illustrated embodiment.

The controller 20 includes an input port 70 with an appropriate coupling member, for example a connector to allow an end of the coaxial cable 24 to be communicatively coupled to the controller 20. As noted above, some embodiments may employ other communications pathways between the controller 20 and the antenna 22, hence other types of coupling members or connectors may be employed. The controller 20 may also include a power switch (not illustrated in FIG. 4), for example, positioned on a back or rear of the controller 20. The controller 20 may further include a power cord (not shown) to couple the controller 20 to a suitable power supply. The power supply may, for example take the form of a standard wall outlet or any other power supply or source. The controller 20 may further include one or more user interface devices for providing information to a user. For example, the controller 20 may include one or more visual indicators 134, for instance one or more light emitting diodes (LEDs) and/or liquid crystal displays. Additionally, or alternatively, the controller 20 may include one or more speakers 130 or other transducers operable to produce sound or tactile sensations. The controller 20 forms a transmitter and receiver, or transceiver, to transmit interrogation signals and receive responses to those signals, as well as to receive electromagnetic signals which may be indicative of noise.

Figure 5:
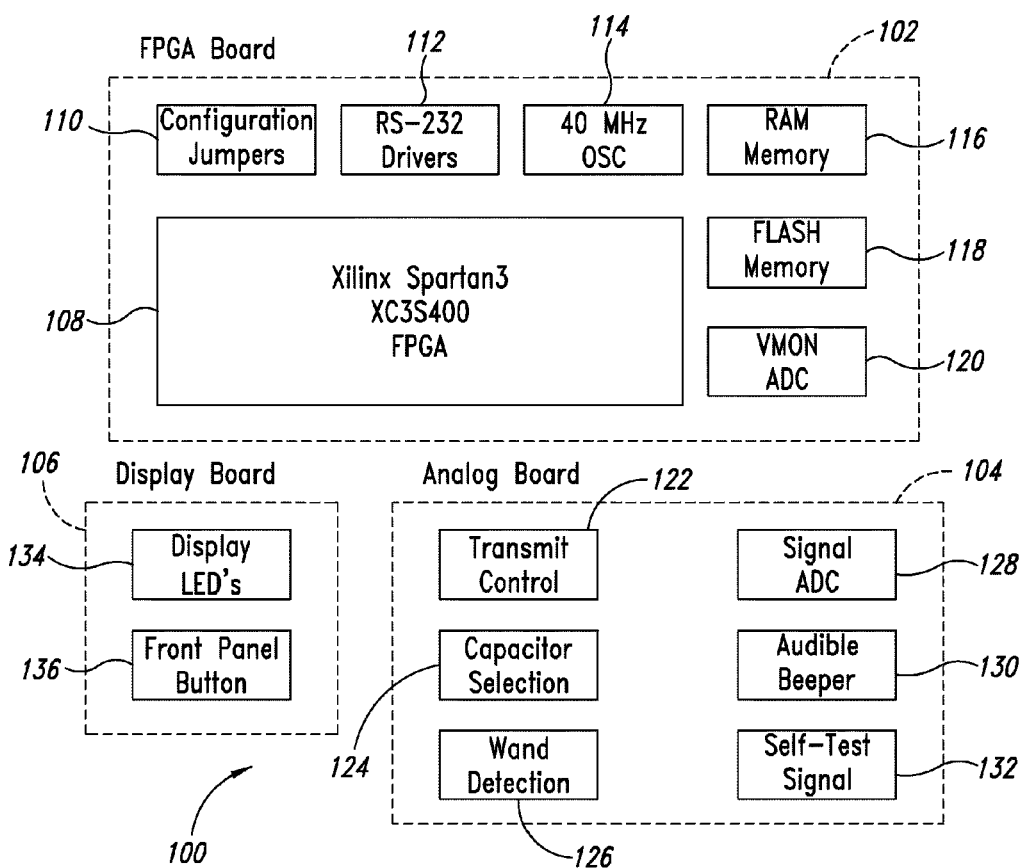
FIG. 5 is a schematic diagram of a control system of the interrogation and detection system, according to one illustrated embodiment.

FIG. 5 shows a control system 100 of the interrogation and detection system 14, according to one illustrated embodiment.

The control system 100 includes a field programmable gate array (FPGA) board 102, analog board 104 and display board 106, communicatively coupled to one another.

The FPGA board includes an FPGA 108, configuration jumpers 110, RS-232 drivers 112, oscillator 114, random access memory (RAM) 116, flash memory 118, and voltage monitoring (VMON) analog-to-digital converter (ADC) 120.

The FPGA 108 may take the form of a Xilinx Spartan3 FPGA, which runs FPGA and application software. As explained below, on power up, the FPGA reads the configuration information and application software program from the flash memory 118.

The configuration jumpers 110 are used to select the application software configuration.

The RS-232 drivers 112 are used to allow the application software to communicate using serial RS-232 data for factory test and diagnostics.

The oscillator 114 sets the clock frequency for the operation of the FPGA 108. The oscillator 114 may, for example, take the form of 40 MHz oscillator, although other frequencies are possible.

The RAM 116 is connected to the FPGA 108 and is available for use by the application software. The application software uses this memory space for storage of both the executable program and program data. The RAM 116 may, for example, have a capacity of 1 MB.

The flash memory 118 contains both the FPGA configuration data and the binary application program. On power up the FPGA 108 reads the flash memory to configure the FPGA 108 and to copy the application program binary data from the flash memory 118 to the RAM 102.

The voltage monitor ADC 120 is connected to the FPGA 108 and controlled by the application software to monitor a power supply and regulated voltage forms in controller electronics.

The analog board 104 includes transmit control circuits 122, capacitor selection circuits 124, wand detection circuit 126, signal ADC 128, audible beeper 130 and self-test signal 132.

Figure 7A:
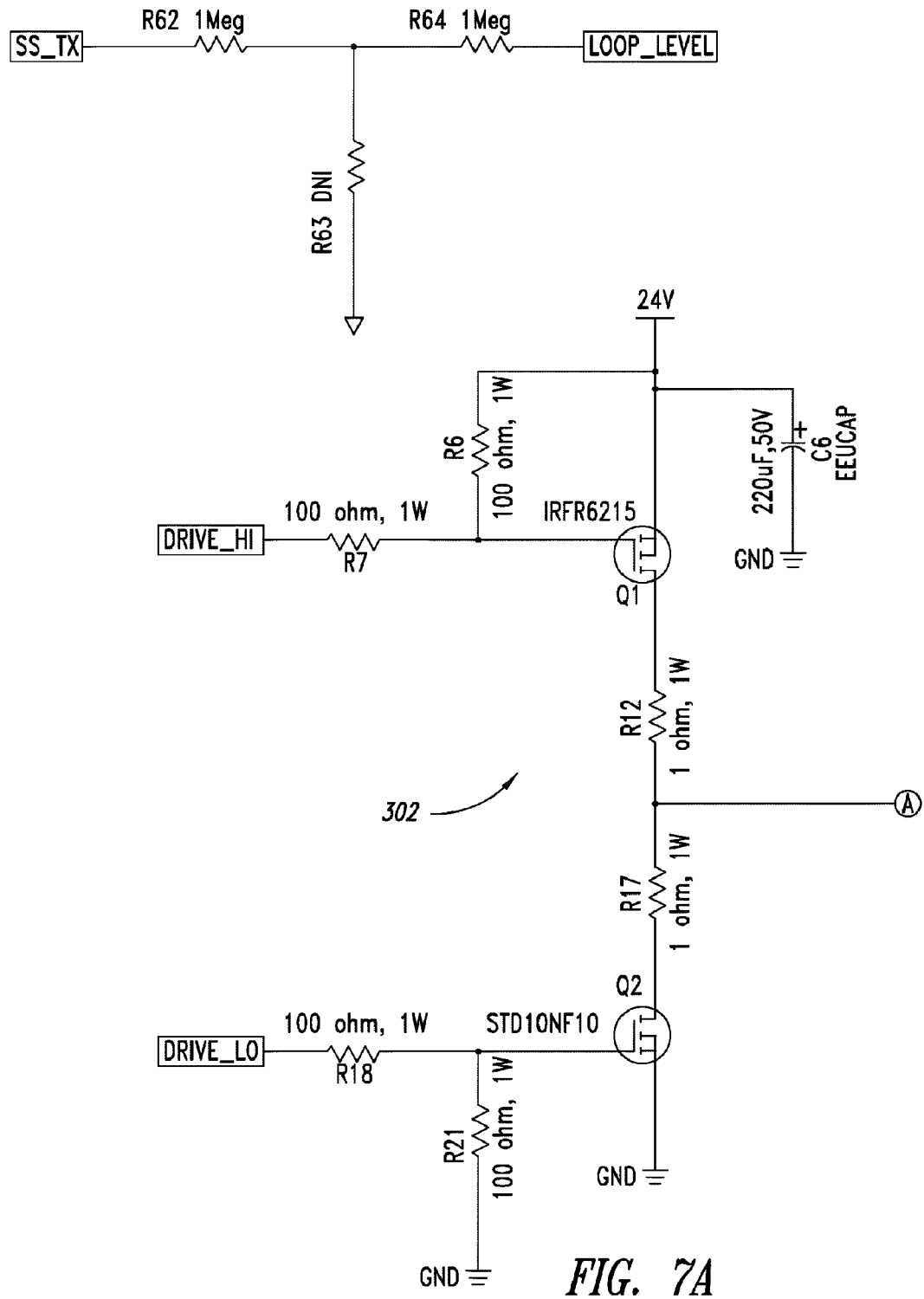
FIGS. 7A-7I are an electrical schematic diagram of the interrogation and detection system including a control circuit and antenna, according to one illustrated embodiment.
Figure 7B:
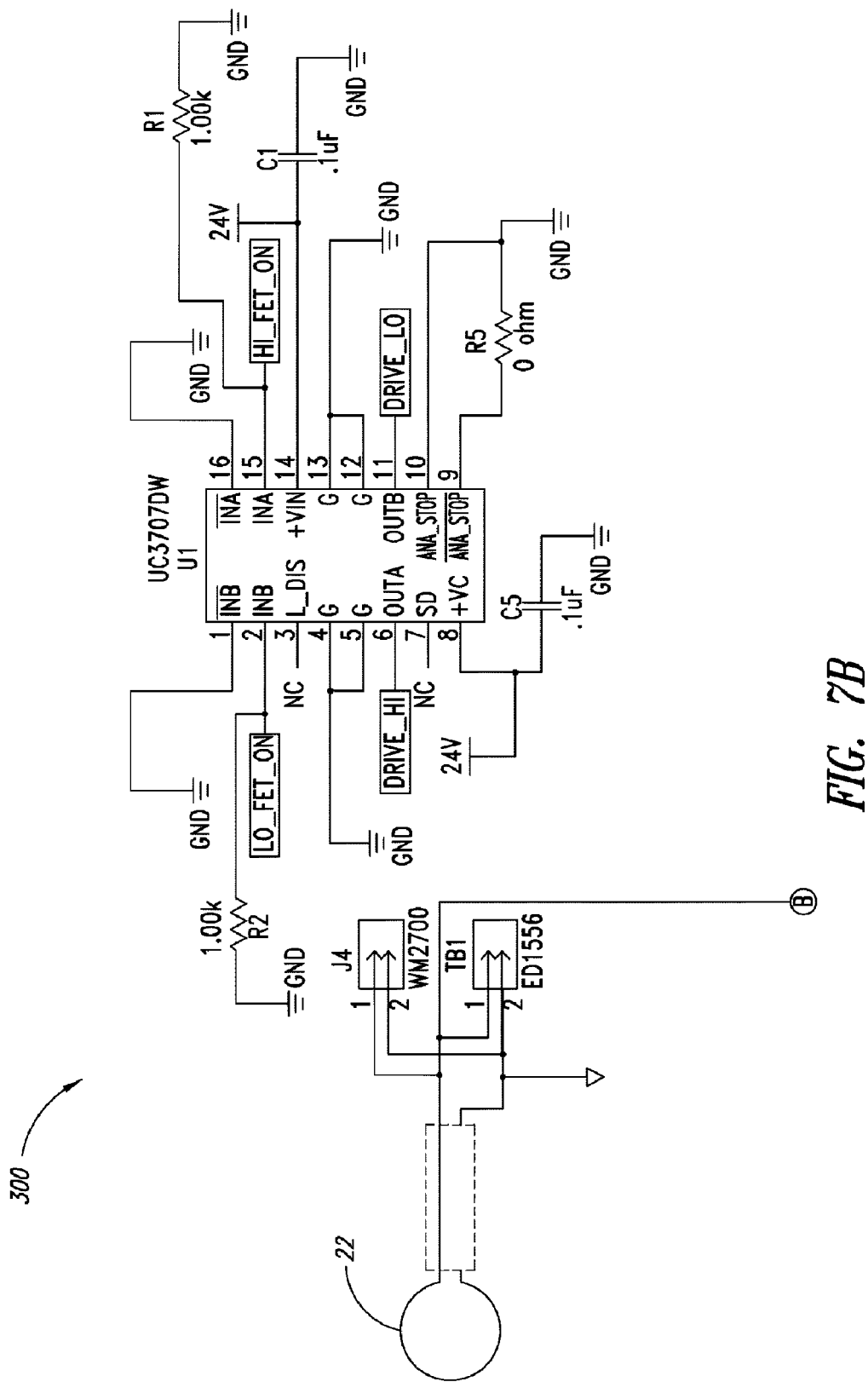
Figure 7C:
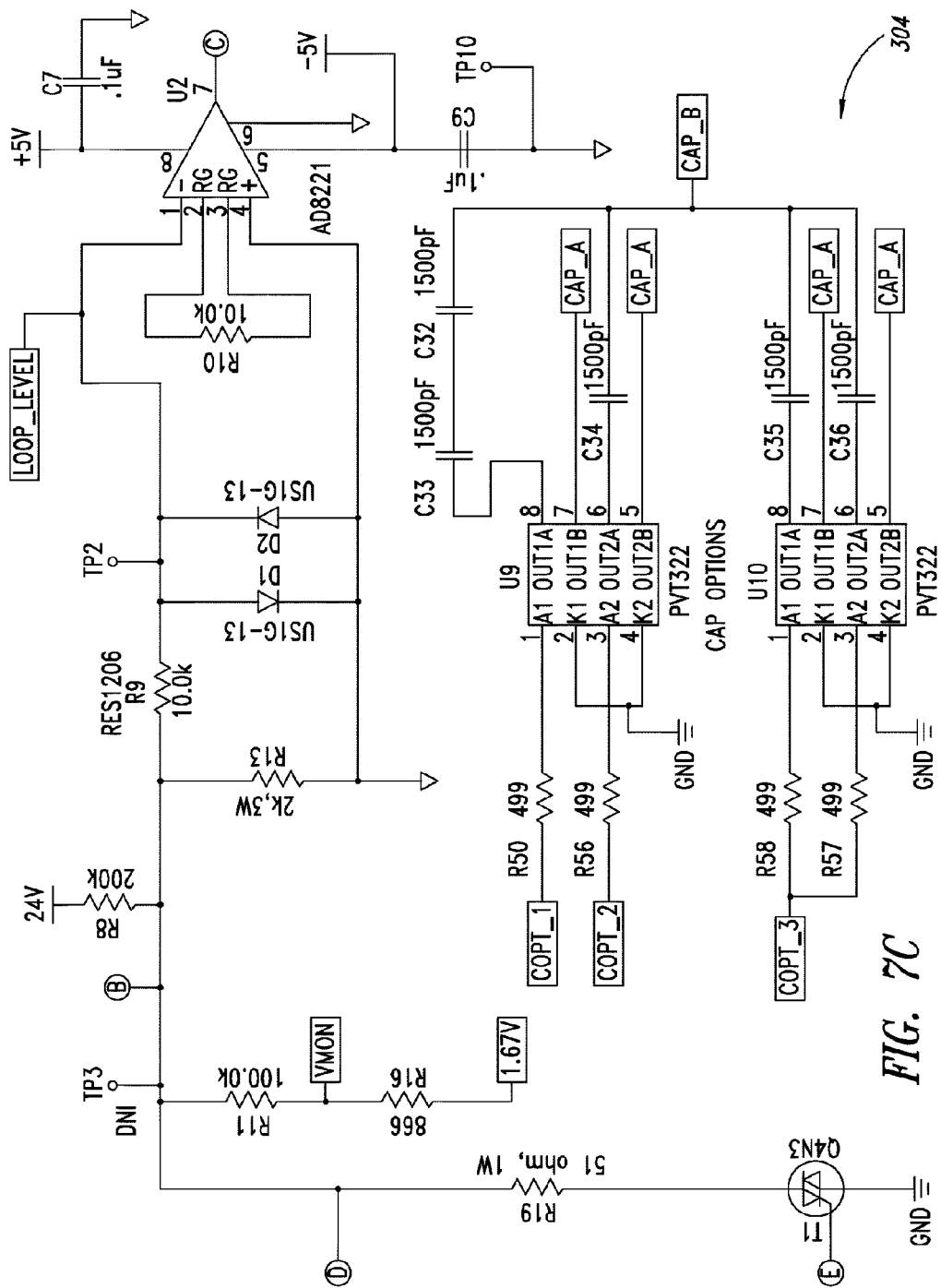
Figure 7D:
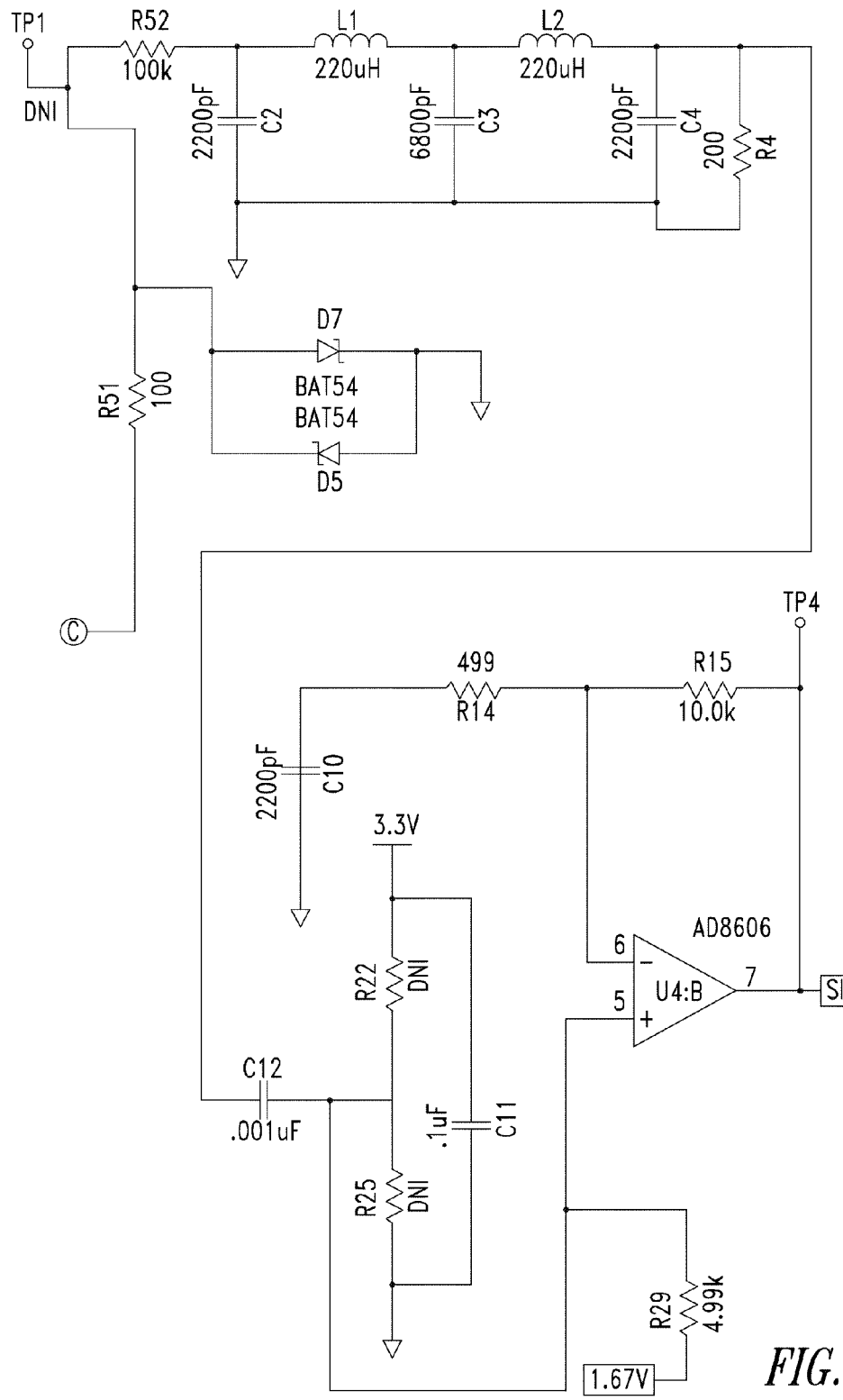
Figure 7E:
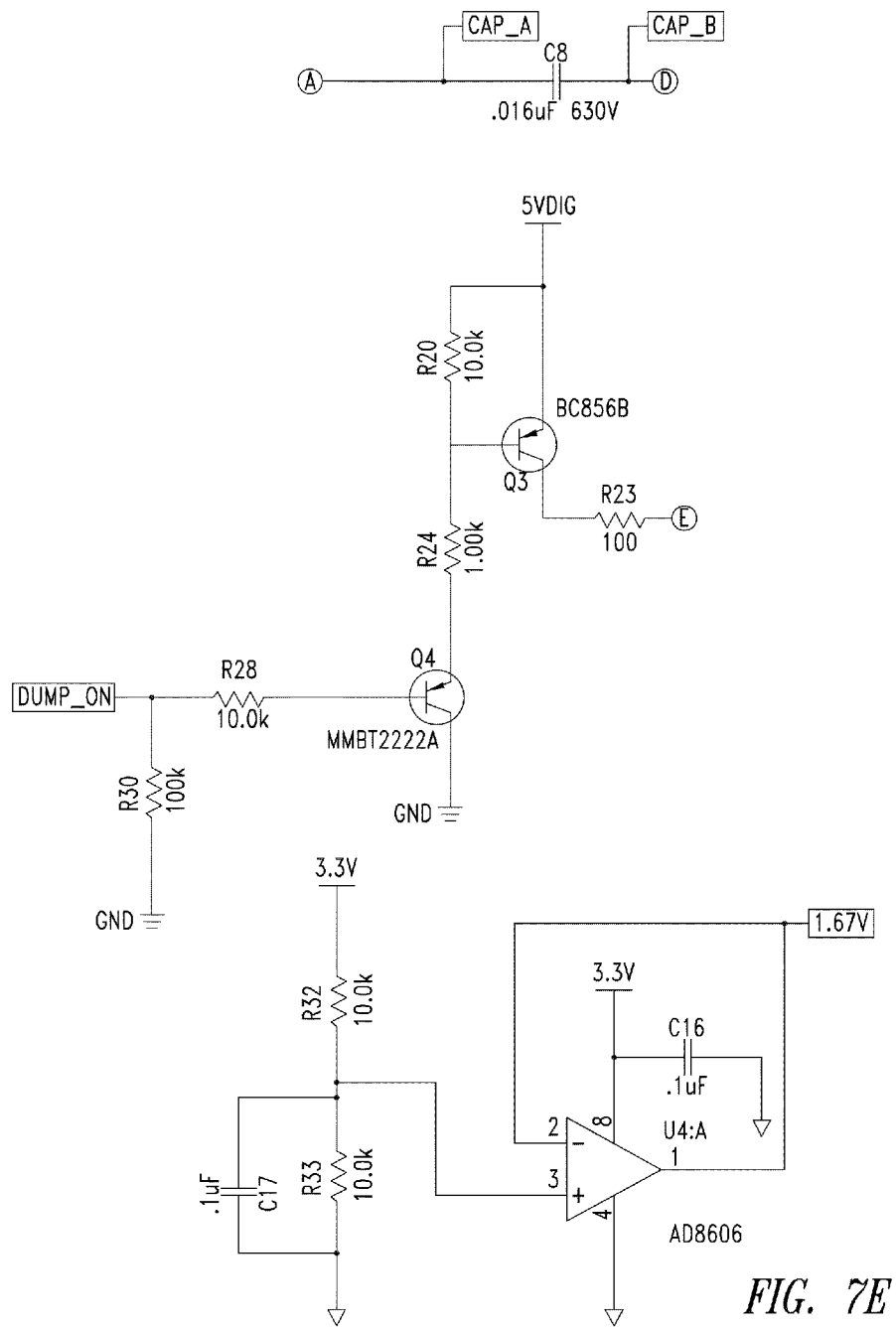
Figure 7F:
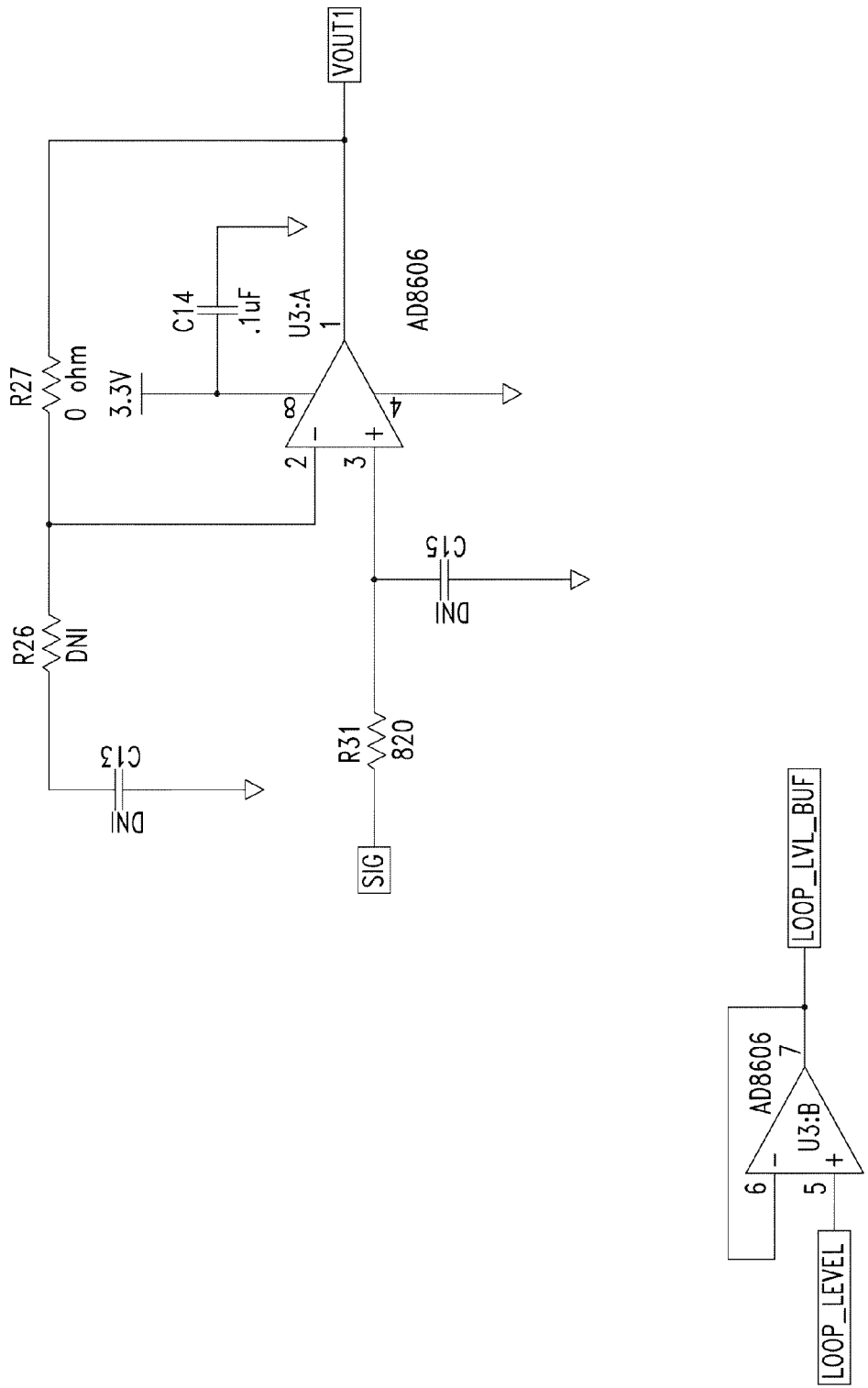
Figure 7G:
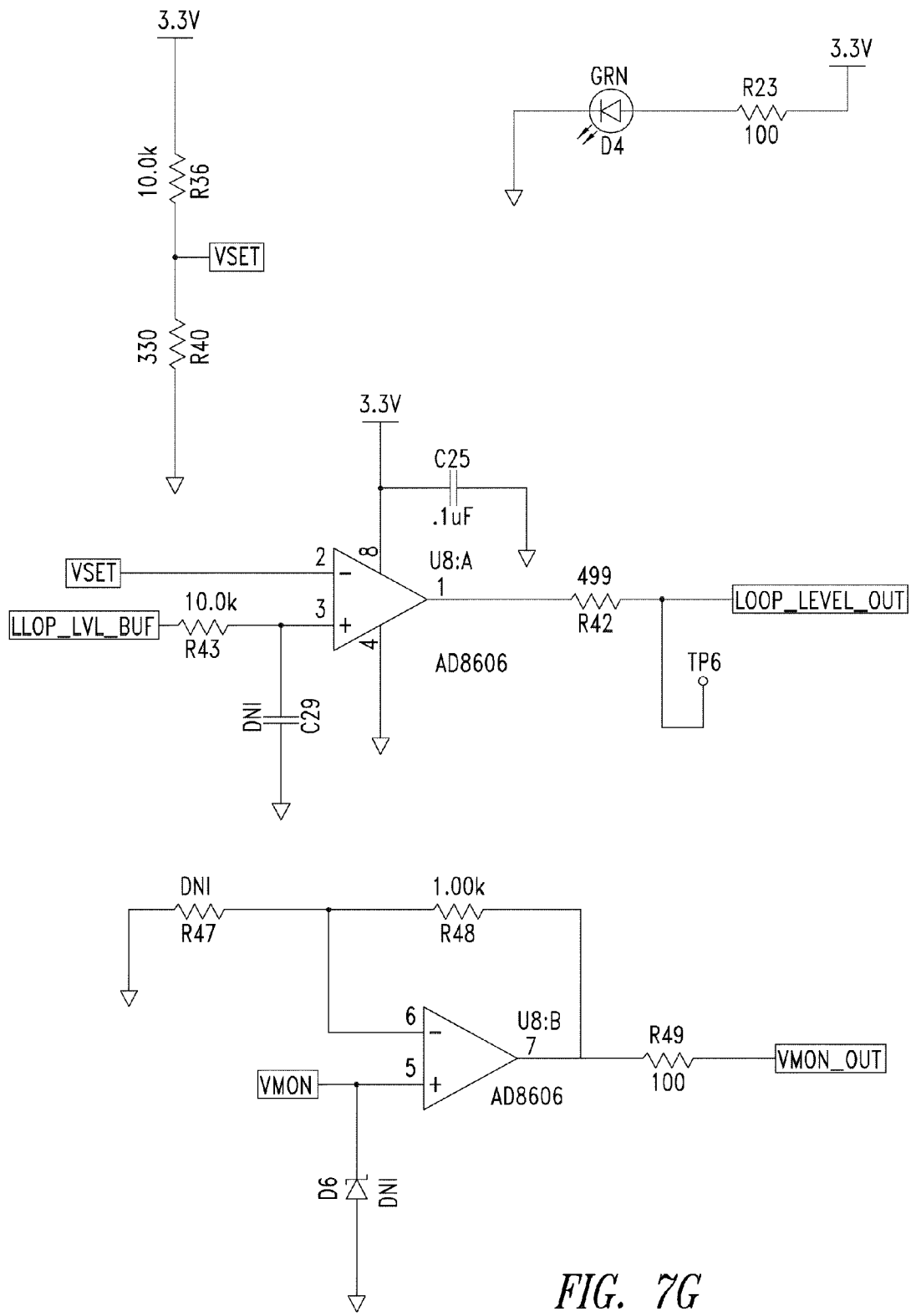
Figure 7H:
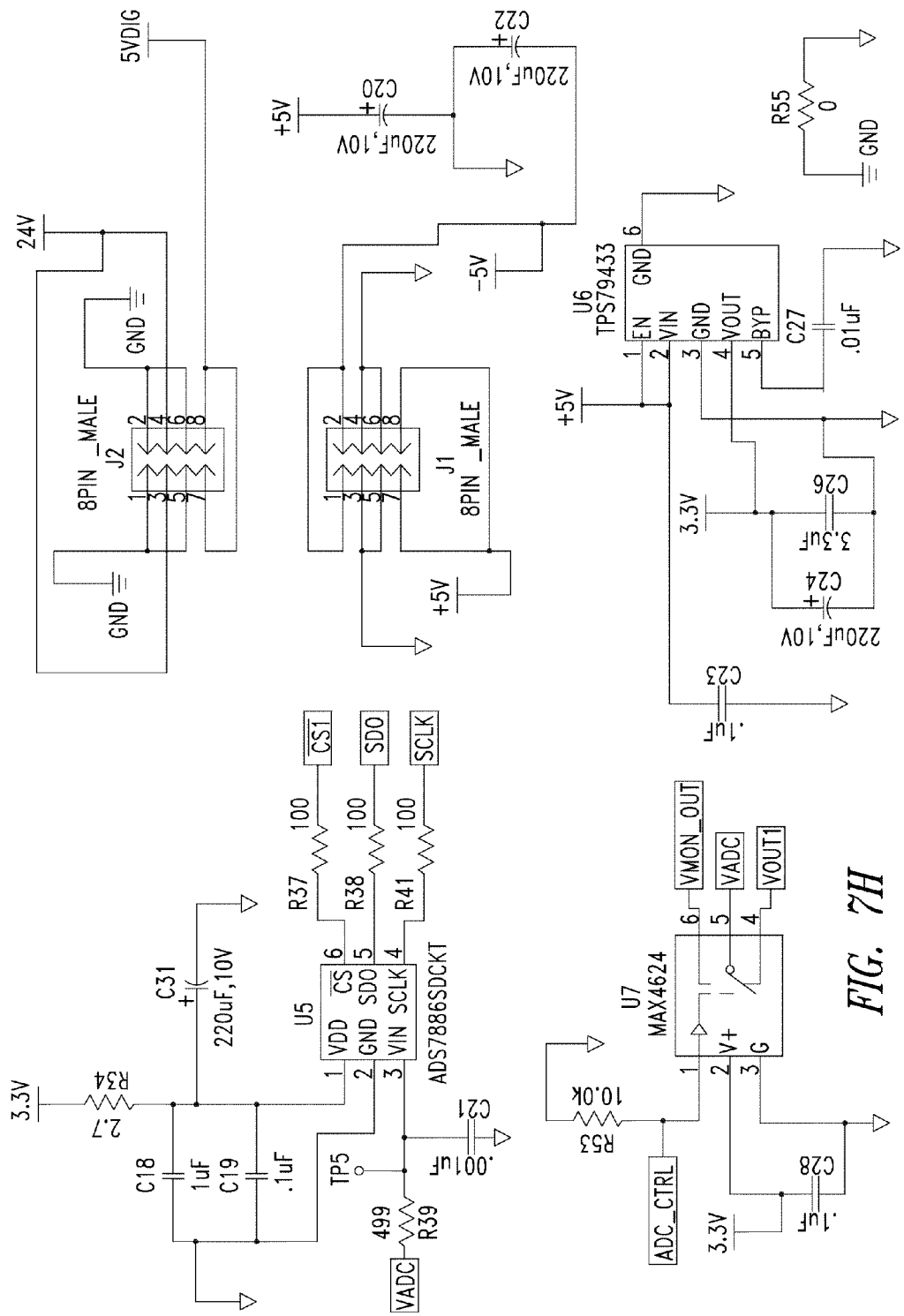
Figure 7I:
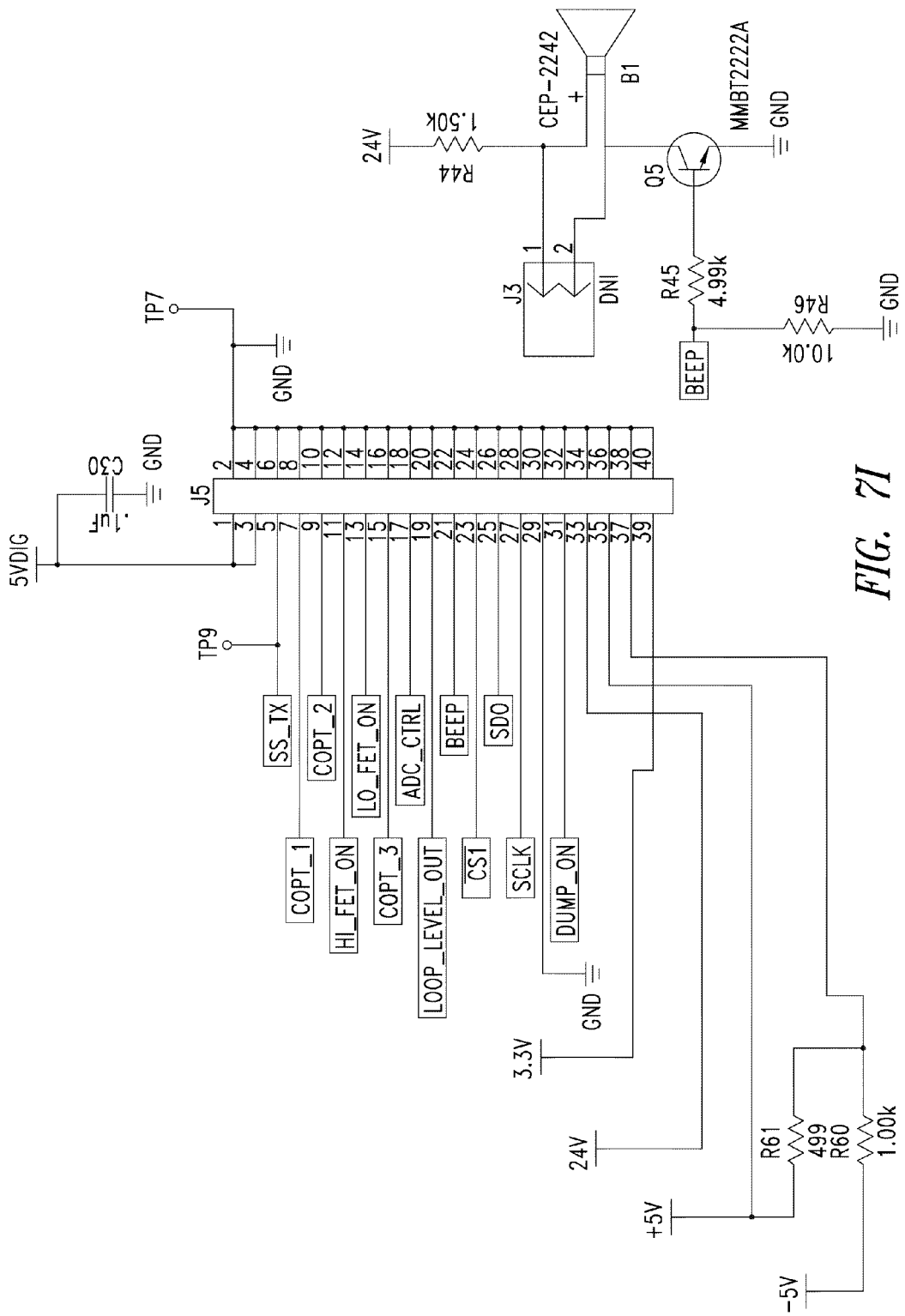

The transmit control circuits 122 on the analog board 104 are controlled by signals from the FPGA 108 to generate a transmit waveform. These signals are denominated as LO_FET_ON and HI_FET_ON, which control the transmit or drive transistors Q1, Q2 (FIG. 7A) along with a signal denominated as DUMP_ON which controls a dump TRIAC (FIG. 7A).

Optional capacitor selection circuits 124 on the analog board 104 are controlled by the signals from the FPGA 108 to tune the drive circuit to match an inductance of the antenna 22.

The wand detection circuit 126 detects when a wand 22a is connected to the controller 20. The output of the wand detection circuit 126 drives a signal denominated as the LOOP_LEVEL_OUT signal, which is an input to the FPGA 108.

The signal ADC 128 is used as a receiver to sample the signals received at the antenna 22a from the transponders 26 (FIGS. 2A-2C). The signal ADC 128 may, for example, operate at a 1 MHz sample rate and may have 12-bits of resolution. The FPGA board 102 generates the timing and control signals for the signal ADC 128, which signal are denominated as ADC_CTRL, CS1, SCLK, SD0.

The audible speaker or beeper 130 can be controlled by the FPGA 108 to emit sounds to indicate various states, modes or operating conditions to the medical provider 12 (FIG. 1).

The FPGA 108 can cause the generation of the self test signal 132 on the analog board 104 at the signal ADC 128. Self-testing may be performed at start up, and/or at other times, for example periodically or in response to the occurrence of certain conditions or exceptions.

The display board 106 includes user interface elements, for example a number of light emitting diodes (LEDs) 134. The FPGA board 102 can control the LEDs 134 on the display board 106. The display board 106 also includes a user selectable activation switch, denominated as front panel button 136. The front panel button 136 is connected to the display board 106 which allow the FPGA 108 to monitor when the front panel button 136 is activated (e.g., pressed).

Figure 6:
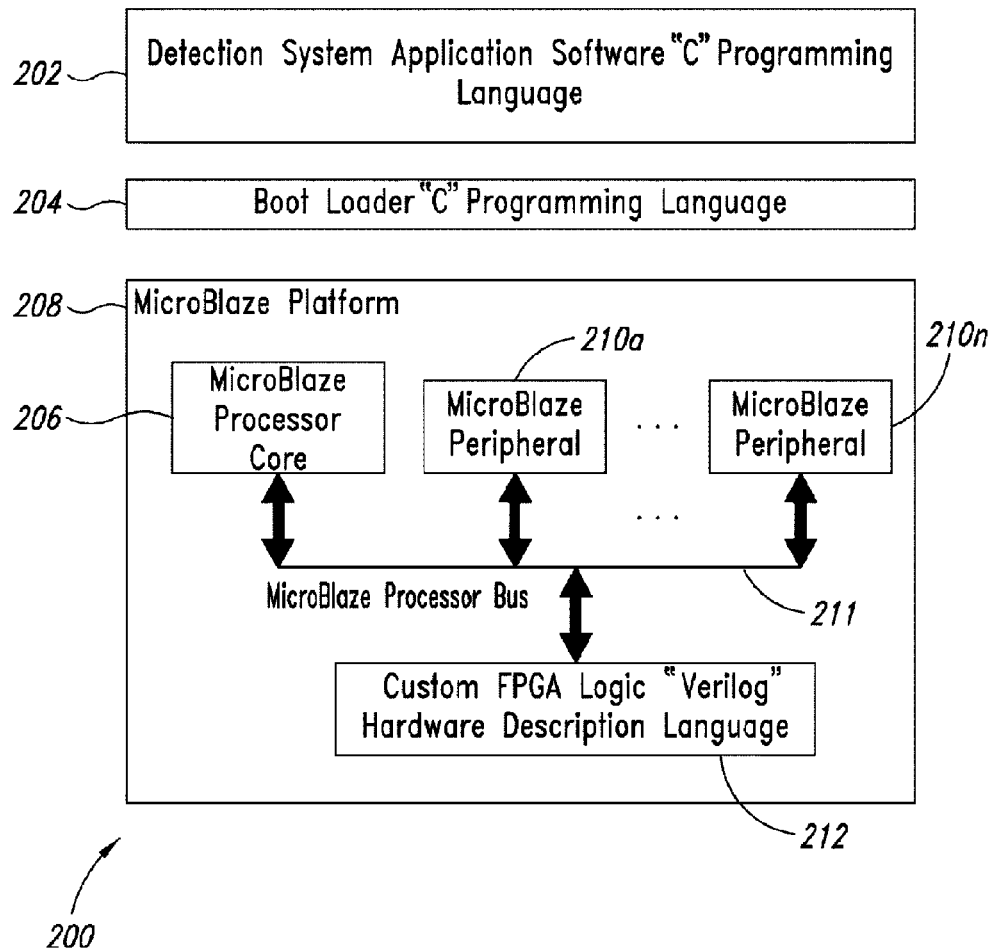
FIG. 6 is a schematic diagram of a software configuration of the interrogation and detection system, according to one illustrated embodiment.

FIG. 6 shows a software configuration 200 of the interrogation and detection system 14, according to one illustrated embodiment.

The software may include application software 202 that is responsible for operating the electronics controller 20 (FIGS. 1 and 4). The application software 202 controls the timing for generating transmit pulses, processes sampled data to detect transponders 26 (FIGS. 2A-2C), and indicates status to the user with the display LED's 134 (FIG. 5) on the display board 106 and/or via the audible speaker or beeper 130 on the analog board 104. The application software 202 is stored in the flash memory 118 (FIG. 5) and transferred into the RAM 116 by a boot loader 204.

The boot loader 204 is automatically loaded when the FPGA 108 is configured, and starts execution after a processor core 206 is reset. The boot loader 204 is responsible for transferring the application software 202 from the flash memory 118 to the external RAM 116.

The processor platform 208 is configured into the FPGA 108 (FIG. 5) on power up from the configuration information stored in the flash memory 118. The processor platform 208 implements a custom microprocessor with a processor core 206, peripherals 210a-210n, and custom logic 212.

The processor core 206 may take the form of a soft processor core supplied by XILINX under the name MICROBLAZE, that implements a 32-bit processor including memory cashes and a floating point unit. A soft core processor is one that is implemented by interconnected FPGA logic cells instead of by a traditional processor logic. The processor core 206 is connected to the internal FPGA peripherals 210a-210n using a 32-bit processor bus 211 called the On-Chip Peripheral Bus. The XILINX supplied peripherals for the MICROBLAZE processor core 206 include external memory interfaces, timers, and general purpose I/O.

The custom logic 212 to create the transmit signals, sample the ADC, and accumulate the transponder return signals is designed as a peripheral to the processor core 206. The custom logic 212 is the part of the design of the FPGA 108.

FIGS. 7A-7I show a control circuit 300 according to one illustrated embodiment. The control circuit 300 is used to drive the antenna 22 to excite or interrogate transponders 26 (FIGS. 2A-2C), and to receive or detect and process signals received by the antenna 22 from the transponders 26. Thus, the control circuit 300 forms a transmitter and receiver, or transceiver.

The control circuit 300 includes a transmitter circuit 302 formed by a pair of drive transistors (e.g., field effect transistors) Q1, Q2 operated in a push-pull configuration between a high voltage rail (e.g., 24 V) and a low voltage rail (e.g., GND). The drive transistors Q1, Q2 are responsive to respective drive signals DRIVE_HI, DRIVE_LO, which are applied to the gates of the respective drive transistors Q1, Q2. The drive transistors Q1, Q2 are coupled to the antenna 22 by a non-switched capacitor C8 and the coaxial cable 24. The antenna 22 and capacitor C8, as well as capacitance provided by the coaxial cable 24, form an LC circuit.

Optionally, the control circuit 300 may also include a dynamic tuning circuit 304. The dynamic tuning circuit 304 selectively adjusts the capacitance of the LC circuit. In the illustrated embodiment, the dynamic tuning circuit 304 includes a number of switched capacitors C33-C36 and relays U9, U10. The relays U9, U10 are operated to selectively couple the switched capacitors C33-C36 in series with the non-switched capacitor C8, thereby adjusting the LC characteristics of the LC circuit, and allowing fine tuning of the LC circuit around center frequencies or center channels of a number of wide band frequency bands, as described in more detail below.

Figure 8:
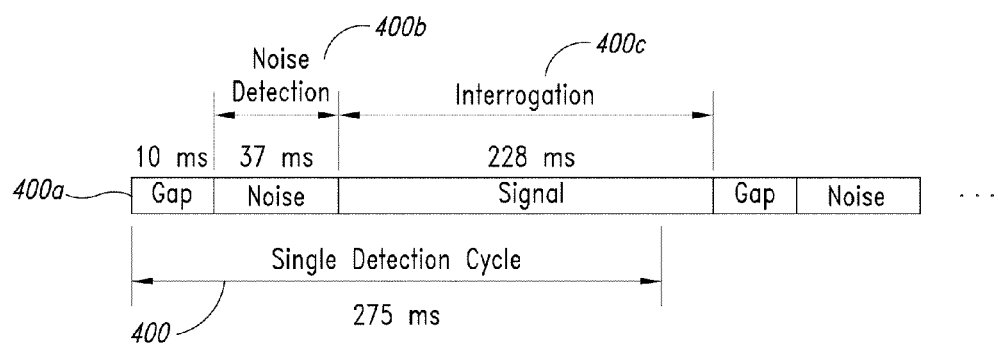
FIG. 8 is a timing diagram illustrating a method of frequency hopping, according to one illustrated embodiment.

FIG. 8 illustrates a detection cycle 400 that employs an approach that optimizes signal to noise ratio (SNR) by a receiver portion, according to one illustrated embodiment. Such may, for example, advantageously increase range or increase sensitivity at a given range.

One embodiment is optimized based on having an overall detection cycle that performs well for transponders with resonant frequencies from approximately 136 KHz to approximately 154 KHz, and which has a pulse timing that is consistent with hardware limitations. An optimal SNR may be achieved by, for example, transmitting a single wideband frequency pulse.

The application software 202 (FIG. 6) implements the detection cycle 400 using transmission or interrogation in a frequency band centered around a center channel or frequency. In the illustrated embodiment, the application software 202 sequences through a non-measurement portion (i.e., gap) 400a, and two distinct measurement portions, denominated as a noise detection portion 400b and an interrogation or signal detection portion 400c, each detection cycle 400. In at least one embodiment, the detection cycle 400 may, for example, be approximately 275 milliseconds, the gap portion may be approximately 10 milliseconds, the noise portion approximately 37 milliseconds and the interrogation or signal portion approximately 228 milliseconds.

During the noise detection portion 400b, which may, for example be a first measurement portion of each detection cycle 400, ambient or background noise is measured or sampled, providing a value indicative of a level of ambient or background noise for the particular environment. The noise measurements or samples are taken or captured at a time sufficiently after excitement of the transponders 26 by the interrogation signal emitted by the transmitter such that the transponders 26 are substantially not resonating or responding to any previous excitation by interrogation signals. In particular, a number N of measurements or samples are taken during the noise detection or first measurement portion 400b.

During the interrogation portion 400c, which may, for example take the form of the second measurement portion of each detection cycle 400, responses by transponders 26 are measured or sampled. The response measurements or samples are taken with the transmitter transmitting or at a time sufficiently close to excitement of the transponders 26 by the interrogation signal emitted by the transmitter such that the transponders 26 are still substantially resonating or responding to the interrogation signal. In particular, a number M of measurements or samples are taken during the interrogation or second measurement portion 400c.

While the interrogation portion 400c is illustrated as one contiguous or continuous portion 400c, in some embodiments the interrogation portion 400c may take the form of two or more separate portions or intervals. Each of the portions 400c may employ the same transmit frequency band, for example centered around 145 KHz. Other center channels or frequencies may for example be 136 KHz, 139 KHz, 142 KHz, 145 KHz, 148 KHz, 151 KHZ and/or 154 KHz, or any other frequency suitable for exciting the transponder to resonate. Some embodiments may employ frequency hopping, for example transmitting a different center channel or frequency for each of a plurality of interrogation portions 400c of each detection cycle 400. Such is discussed further in U.S. provisional patent application Ser. No. 60/892,208, filed Feb. 28, 2007 and U.S. non-provisional application Ser. No. 11/743,104, filed May 1, 2007.

The gap portion 400a may provide time for the response of the transponders 26 to the interrogation signal to decay sufficiently to allow measurement of noise.

Some embodiments may arrange the gap 400a, the noise detection portion 400b and/or the interrogation portion 400c, or parts thereof, in a different order.

In one embodiment, the time to accumulate the noise sample or value indicative of a noise level may, for example, be approximately 37 milliseconds, and the time to accumulate the transponder signal measurement approximately 228 milliseconds. Along with a gap 400a of approximately 10 milliseconds between the signal and noise portions, the time for a single detection cycle 400 would be approximately 275 milliseconds. As noted above, the transmitter is OFF during the noise measurement portion 410b of each detection cycle to allow the receiver to measure ambient noise, and the signal measurement portion 410c is taken with the transmitter transmitting a wideband interrogation signal about the particular center channel or frequency.

The noise samples collected by the receiver may be accumulated and a highest one or more of multiple samples or measurements over one or more detection cycles selected or used to prevent unwarranted fluctuations. The noise level may be determined by a noise level determiner, which may be implemented as part of the controller or as a dedicated circuit, and which may be implemented as a hardwired circuit or as a programmed circuit which may include a processor or other programmable element (e.g., FPGA, ASIC). The response signals from the transponder 26 may be accumulated and/or averaged or integrated over one detection cycle or over multiple detection cycles.

The number N of noise measurements or samples and/or the number M of response measurements or samples may be selected to achieve a desired ratio of N to M, in order to achieve or maintain a desired signal to noise ratio. For example, obtaining 200 noise measurements or samples and 800 response measurements or samples each detection cycle results in an SNR of approximately 2 (e.g., the square root of the 800 divided by 200). While an SNR as low as 1.1:1 may be sufficient in some embodiments, an SNR approaching 2:1 ensures sufficient differentiation to eliminate or reduce the possibility of false positives to an acceptable level for the particular applications envisioned herein. Any known hardware and software accumulators, summer, integrators and/or other hardware or software may be suitable.

Figure 9:
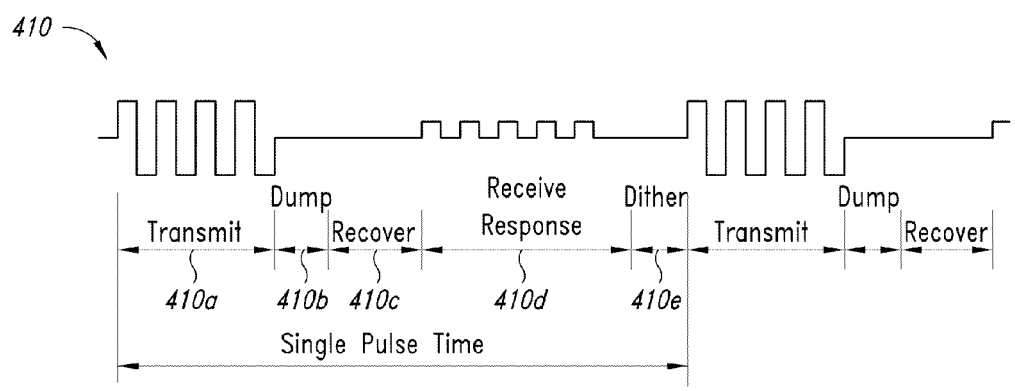
FIG. 9 is a timing diagram illustrating pulsed timing, according to one illustrated embodiment.

FIG. 9 illustrates pulse timing, according to one illustrated embodiment.

The custom logic in the FPGA 108 generates the timing and control signals for each pulse 410. During a transmit portion 410a of the pulse 410, the logic of the FPGA 108 drives the drive transistor control lines to generate the transmit signal. The FPGA logic controls the frequency of the transmit signal. During a dump portion 410b of the pulse 410, the logic of the FPGA 108 drives the gate of the dump TRIAC T1 to quickly drain the transmit energy from the antenna 22 in order to allow detection of the response signal form the transponder 26, if any. A recovery portion 410c of the pulse 410 implemented by the controller allows receive filters and amplifiers to recover from the transmitted pulse before detecting the response signal from the transponder 26, if any. During the receive response portion 410d of the pulse 410, the FPGA 108 controls the signal ADC 128 to sample the response signal from the transponder 26, if any. The signal ADC 128 may, for example, sample at a 1 MHz sample rate with a 12-bit resolution. A dither portion 410e of the pulse 410 implemented by the controller has a random variable length of time, and may, for example be generated by a pseudo-noise (PN) sequence generator. Adding a random length of time between pulses de-correlates the response signal received from the transponder 26 from constant frequency sources of interference, if any.

For example, within each of 228 millisecond signal measurement intervals 400c discussed above, the custom logic of the FPGA 108 (FIG. 5) accumulates the received signals from, for example 800 pulses.

Figure 10:
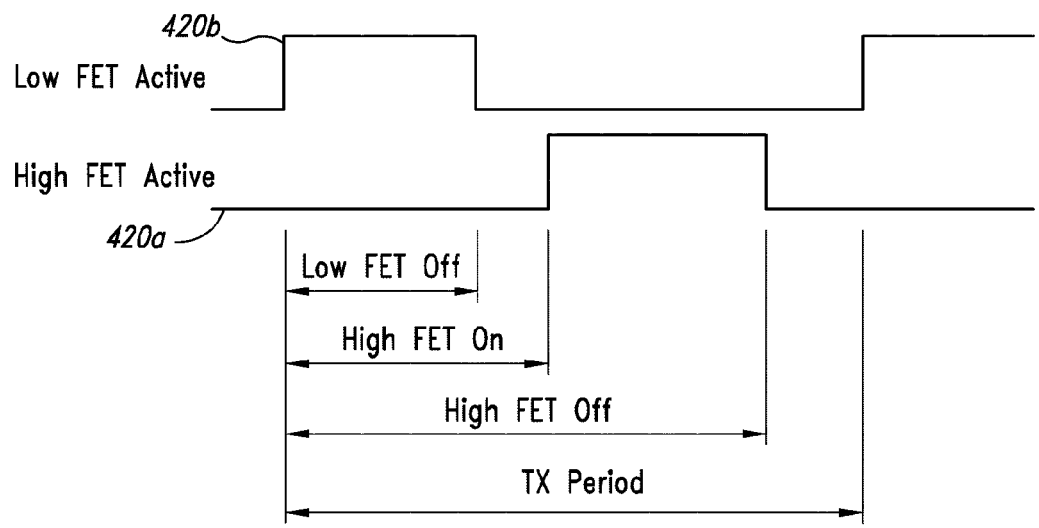
FIG. 10 is a timing diagram showing activation of a pair of transistors of the control circuit in a push-pull configuration to drive the antenna, according to one illustrated embodiment.

FIG. 10 shows signal timing for driving the drive transistors Q1, Q2 (FIG. 7A), according to one illustrated embodiment.

The custom logic in the FPGA 108 (FIG. 5) generates the signals 420a, 420b to drive the drive transistors Q1, Q2 (FIG. 7A) during the transmit portion 410a (FIG. 9) of the pulse 410. A transmit (TX) period value is used by the logic of the FPGA 108 to set the transmit frequency. The low transistor (e.g., Low FET) Q2 turns ON at the beginning of the transmit period. The Low FET off value controls when the low transistor (e.g., Low FET) Q2 is turned OFF. The low transistor Q2 is turned OFF before the high transistor (e.g., High FET) Q1 is turned ON to avoid a short circuit through the transistors Q1, Q2. The High FET on value controls when the high transistor (e.g., High FET) Q1 is turned ON. The High FET Off value controls when the high transistor Q1 is turned OFF. The high transistor is turned OFF before the low transistor Q2 is turned ON to avoid a short circuit through the transistors Q1, Q2. For example, to achieve a transmit frequency of 144.9 KHz, the transmit period should be set to 6.9 psec. Also for example, a suitable duration that both the low and high transistors Q1, Q2 are OFF may be set to 400 nsec.

The ADC converts the signal received from the transponder 26, if any, from analog to digital. Such conversion may, for example, be performed at a sampling rate of 1 MHz with a 12-bit data resolution. The sampled ADC data is then accumulated together or integrated, for example over 800 measurements or samples, to compute the total summed response signal received from the transponder 26, if any.

The accumulated or integrated received signal is match filtered with both in-phase and quadrature reference signals to determine the signal magnitude. The received receive signal is matched filtered with a plurality of reference signals, for example with the seven reference signals, for instance as shown in Table 1 below. Some embodiments, may employ match filtering before accumulating or integrating the received signal.

TABLE 1

| Match Frequency |
| --- |
| 136 KHz |
| 139 KHz |
| 142 KHz |

TABLE 1-continued

| Match Frequency |
| --- |
| 145 KHz |
| 148 KHz |
| 151 KHz |
| 154 KHz |

The maximum value for the matched filters (e.g., seven matched filters) with active transmit is compared with an adjusted detection threshold by a comparator. If the maximum value is greater than the detection threshold, then a response signal from a transponder 26 is considered as having been detected by the presence or absence determiner, and appropriate action is taken, such as discussed below with reference to FIG. 17. Noise filtering is further discussed further below, with reference to FIG. 16. The comparator may be part of the controller and/or the presence or absence determiner and may be implemented as part of the controller or as a dedicated circuit, and which may be implemented as a hardwired circuit or as a programmed circuit which may include a processor or other programmable element (e.g., FPGA, ASIC).

Noise faults may be detected as well as wand transmit voltage faults. Noise faults may be detected when the matched filter output during the noise detection portion is greater than a noise fault threshold (e.g., a threshold magnitude 2.7 mV over a threshold time, e.g., 7 seconds or threshold magnitude 7 mV over a time threshold of 7 seconds). Wand transmit voltage faults may be detected when the wand transmit voltage drops below a wand voltage fault threshold (e.g., 270 $V_{Peak-to-Peak}$). Two environmental faults in a row such as the above, may trigger an Environmental Error Mode, while two normal measurements in a row may return to a normal Scan Mode. Faults in general are discussed in more detail below. Alternatively, the interrogation and detection system may employ a fast Fourier transform approach (FIG. 34) in lieu of match filtering.

Figure 11:
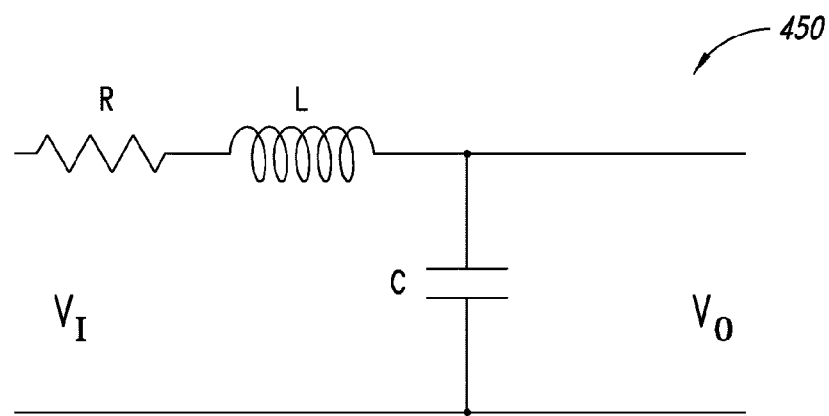
FIG. 11 is a schematic diagram of a model circuit that models how a transponder responds to the transmitted interrogation signals, according to one illustrated embodiment.

FIG. 11 shows a model circuit 450 that models how a transponder responds to the transmitted interrogation signals, according to one illustrated embodiment.

The model includes a resistance R in series with an inductance L on one voltage rail, and a capacitance C coupled across the voltage rails. An input voltage $V_I$ and an output voltage $V_O$ are produced across the voltage rails.

The Laplace transform for the transponder response model are represented by equations 1 and 2.

$$V_O(s) = H(s)V_I(s) \quad \text{Equation 1}$$

$$H(s) = \left(\frac{1}{LC}\right)\frac{1}{s^2 + \frac{R}{L}s + \frac{1}{LC}} \quad \text{Equation 2}$$

Using the Laplace equations, the transponder response output can be simulated for various input signals. The simulated and measured transponder responses are shown in FIGS. 12-15.

Figure 12:
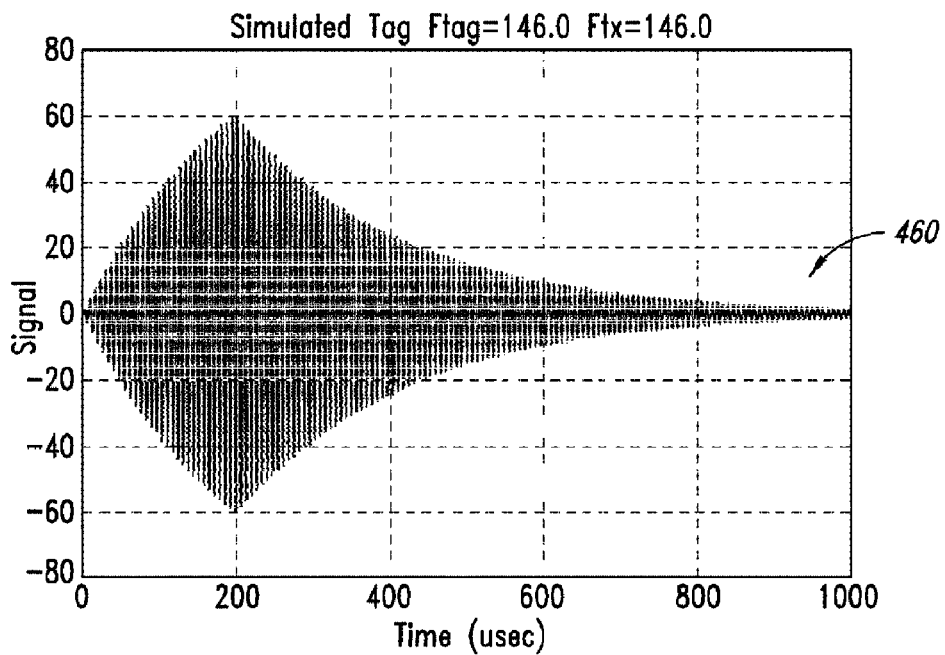
FIG. 12 is a graph of a simulated transponder response signal based on the model circuit of FIG. 11 where a frequency of the response signal matches a frequency of the interrogation signal, according to one illustrated embodiment.

FIG. 12 shows a graph of a simulated transponder response signal 460 based on the model circuit 450 (FIG. 11), according to one illustrated embodiment.

The simulated transponder response signal 460 is produced by the transponder in response to excitation by an interrogation signal. The simulated transponder response signal 460 represents a response by the transponder at the same frequency as the frequency of the interrogation signal (e.g., 146 KHz).

Figure 13:
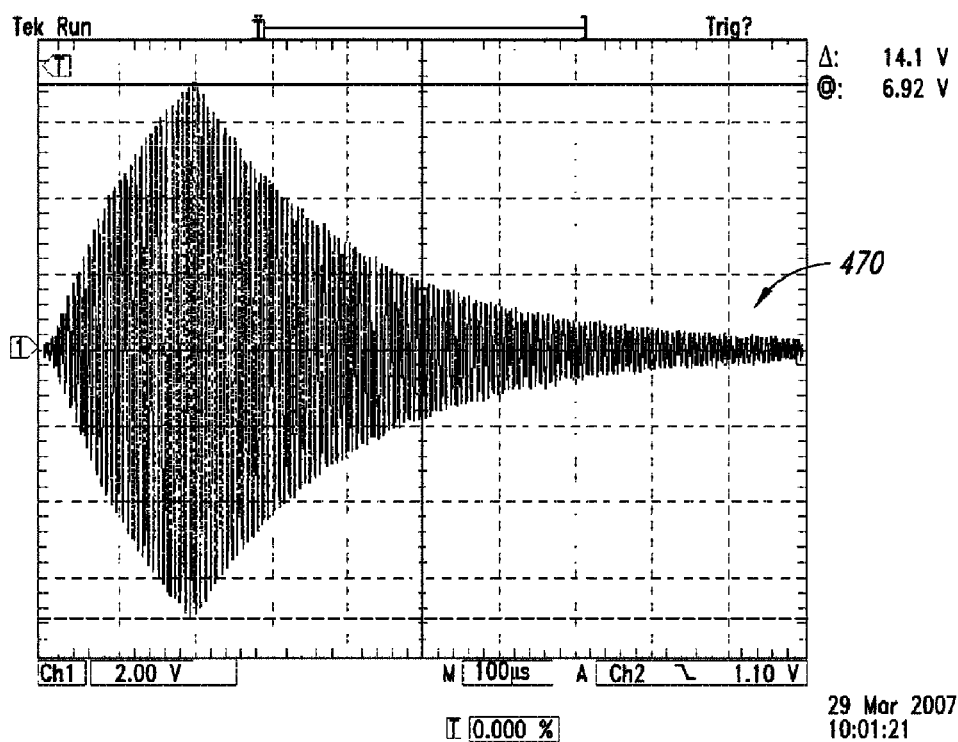
FIG. 13 is a graph of a measured transponder response signal where a frequency of the response signal matches a frequency of the interrogation signal, according to one illustrated embodiment.

FIG. 13 shows a graph of a measured transponder response signal 470, according to one illustrated embodiment.

The measured transponder response signal 470 is produced by the transponder in response to excitation by an interrogation signal. The measured transponder response signal 470 represents a response by the transponder at the same frequency as the frequency of the interrogation signal (e.g., 146 KHz).

Figure 14:
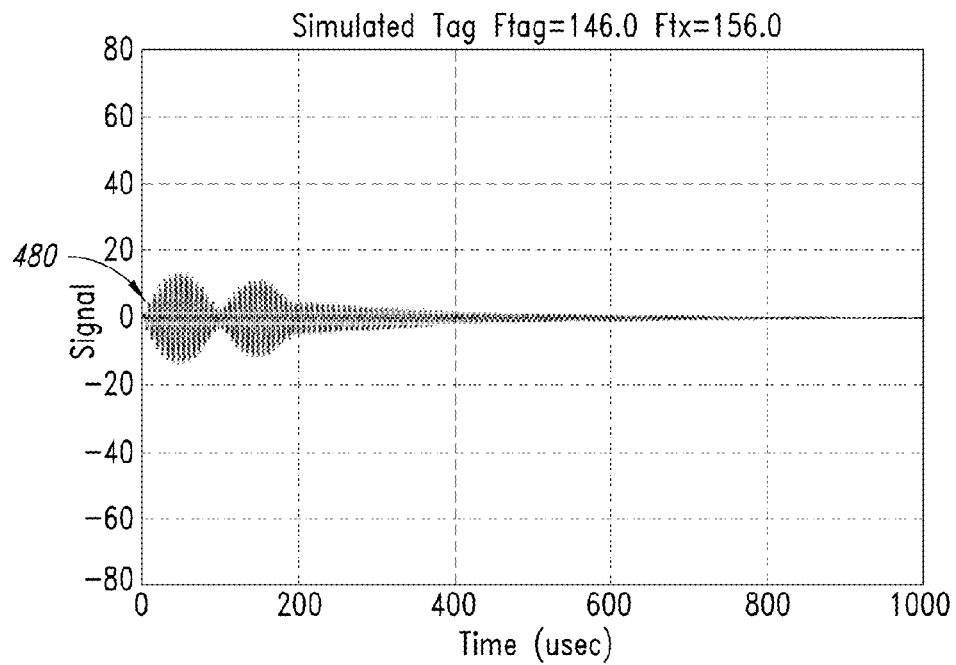
FIG. 14 is a graph of a simulated transponder response signal based on the model circuit of FIG. 11 where a frequency of the interrogation signal is higher than a frequency of the response signal, according to one illustrated embodiment.

FIG. 14 shows a graph of a simulated transponder response signal 480 based on the model circuit 450 (FIG. 11), according to one illustrated embodiment.

The simulated transponder response signal 480 is produced by the transponder in response to excitation by an interrogation signal. The simulated transponder response signal 480 represents a response by the transponder at a frequency (e.g., 146 KHz) to an interrogation signal that has a higher frequency (e.g., 156 KHz), for instance 10 KHz higher than the response signal.

Figure 15:
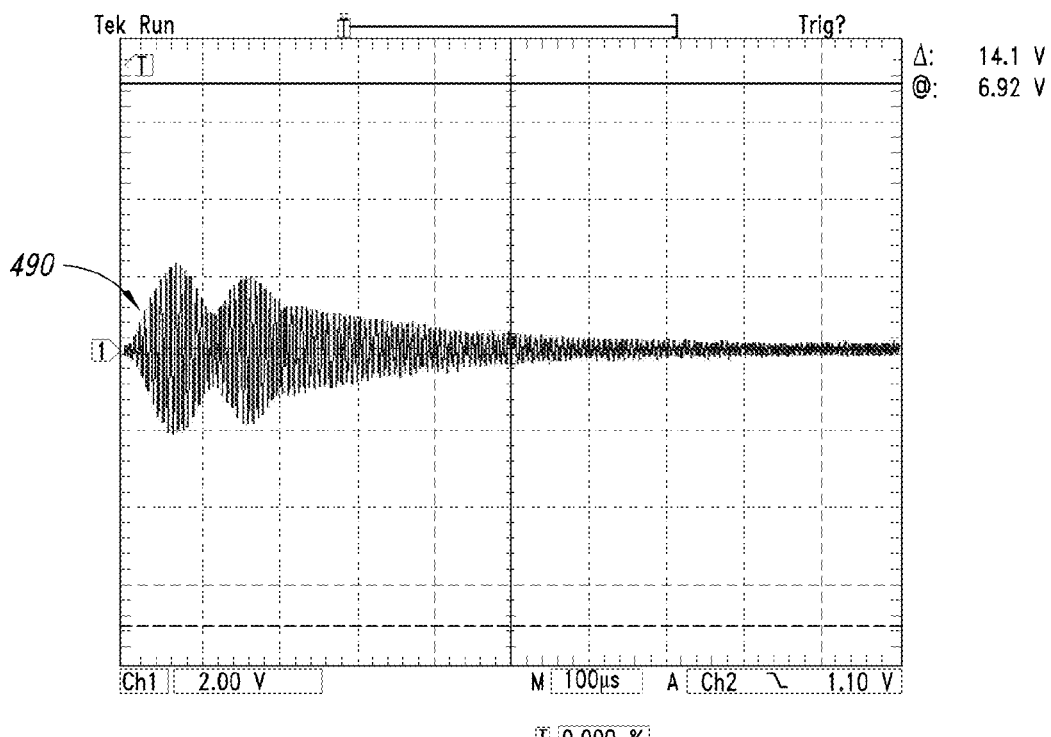
FIG. 15 is a graph of a measured transponder response signal where a frequency of the interrogation signal is higher than a frequency of the response signal, according to one illustrated embodiment.

FIG. 15 shows a graph of a measured transponder response signal 490, according to one illustrated embodiment.

The measured transponder response signal 490 is produced by the transponder in response to excitation by an interrogation signal. The measured transponder response signal 490 represents a response by the transponder at a frequency (e.g., 146 KHz) to an interrogation signal that has a higher frequency (e.g., 156 KHz), for instance 10 KHz higher than the response signal.

The similarity between the simulated transponder response signals 460, 480 and the measured transponder response signals 470, 490 demonstrates that there is a good match using the circuit model 450.

Figure 16:
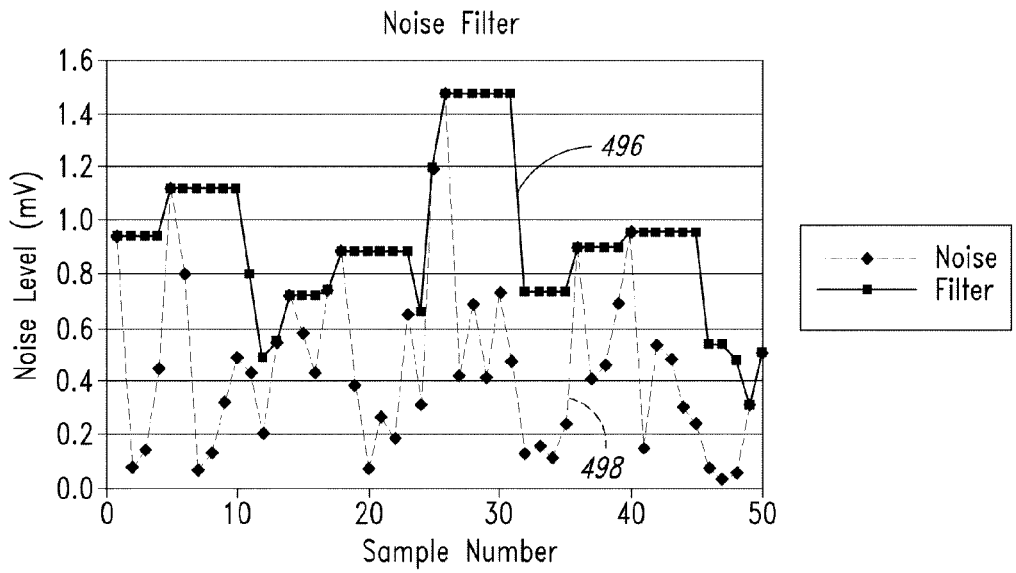
FIG. 16 is a graph showing noise and filter levels for noise filtering, according to one illustrative embodiment.

FIG. 16 is a graph showing an example of measured noise and the output of the noise filter corresponding to the measurements, according to one illustrative embodiment.

The noise filtering processes the measured or sampled noise values for each detection cycle to determine a stable noise floor value. The output of the noise filter may, for example, be the maximum of either the current noise measurement or a decayed value of the previous nose floor.

The output of the noise filter is an estimate of the current noise floor level after selecting the highest of a plurality (e.g., 6) of noise measurements or samples. The filtered noise floor may advantageously include samples collected, captured or measured both before and after a given signal sample is collected, captured or measured. Thus, for any sample of a given detection cycle the noise floor may include noise samples from the given detection cycle, as well as a next successive detection cycle. The filtered noise floor may additionally, or alternatively, include noise samples from one or more successively preceding detection cycles, as well as one or more successfully succeeding detection cycles.

The number of response measurements or samples averaged to create the full signal may, for example, be 800. Using the noise filter output as an adaptive detection threshold of the full signal provides an adaptive threshold that is estimated to be the square root of the quotient of 800 divided by 200, or approximately 2.0 times the estimated noise floor level for the full signal. This provides approximately twice the estimated noise floor. Performance in very low noise conditions may be further stabilized by using an adaptive threshold, implemented by a detection threshold adjuster, that is twice the filtered noise level (e.g., 0.5 mV). The adaptive threshold adjuster may be implemented as part of the controller or as a dedicated circuit, and may be implemented as a hardwired circuit or as a programmed circuit which may include a processor or other programmable element (e.g., FPGA, ASIC).

Figure 17:
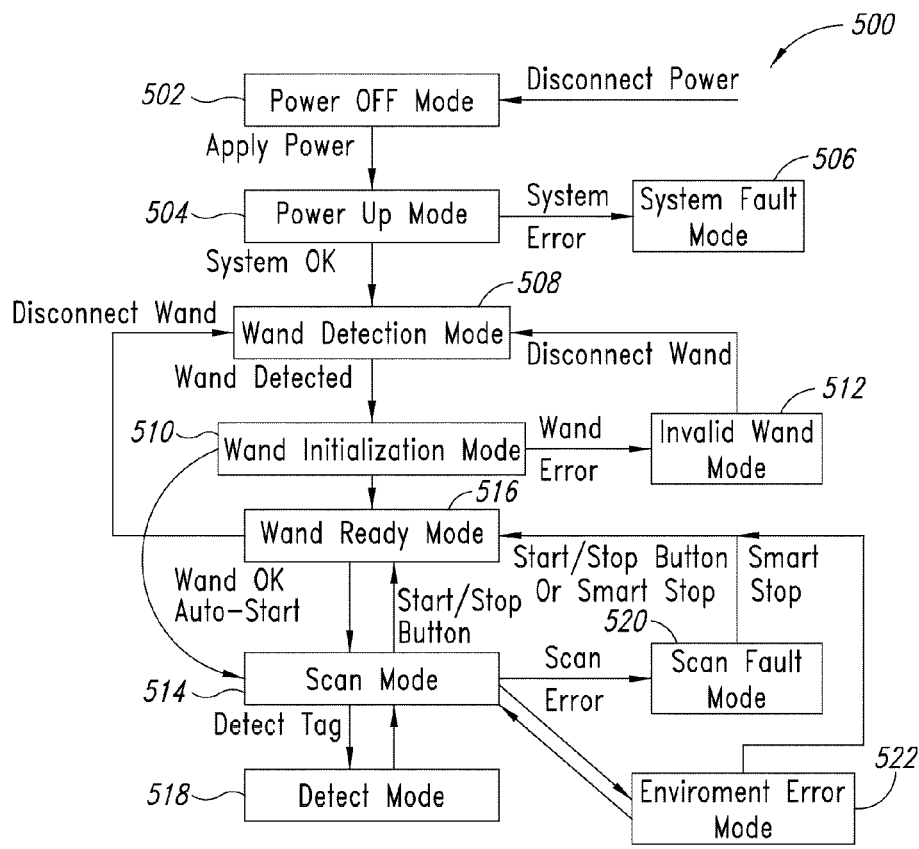
FIG. 17 is a flow diagram of a method of operating an interrogation and control system, according to one illustrated embodiment.

FIG. 17 shows a method 500 of operating the interrogation and detection system 14 according to one illustrated embodiment.

In response to detecting a disconnect of power, the interrogation and detection system 14 enters a Power OFF mode at 502. For example, the Power OFF mode 502 may be entered when the controller 20 (FIGS. 1 and 4) is unplugged or when the power switch on the controller 20 is turned OFF. In the Power OFF mode 502, the Power LED 134a and other front panel LEDs 134 will be turned OFF (non-emitting). The software 200 is inoperative in the Power OFF mode 502.

In response to detecting an application of power, the interrogation and detection system 14 enters a Power-Up mode 504. The Power UP mode 502 may, for example, in response to the application of power to the controller 20 and turning ON the switch on the back of the controller. In the Power-Up mode 504, a Power LED 134a may be turned ON or illuminated, and may remain ON or illuminated as long as the power is applied and the switch is in the ON state. In response to entering the Power UP mode 502, the software 200 will perform software initialization, built in tests, and an audio/visual test.

If a fault is detected, the software 200 progresses to a System Fault Mode 506. If no faults are detected, the software 200 may turn a System Ready LED green, and enter a Wand Detection Mode 508.

In the System Fault mode 506, the software 200 may cause an indication of the detection of a system fault by blinking a System Ready LED 134b yellow, and/or issuing a sequence of rapid beeps or other sounds. The corrective action for the System Fault Mode 506 is to cycle power to reinitiate the Power Up mode 504. Continued failure indicates a failed controller 20.

In the Wand Detection Mode 508, the software 200 checks for a wand 22a connected to the controller 20. The Wand Detection Mode 508 may be indicated by turning the System Ready LED 134b green and turning the Wand Ready LED 134c OFF. If no wand 22a is detected, the software 200 remains in the Wand Detection Mode. If a wand 22a is detected, the software 200 progresses to the Wand Initialization Mode 510.

At the start of the Wand Initialization Mode 510, after the detection of a wand 22a, the software 200 may turn the Wand Ready LED 134c yellow and check for the presence of a fuse in the wand 22a. If a fuse is found, the software 200 may attempt to blow the fuse and verify that the fuse was correctly blown. After the fuse is blown the software 200 may verify that wand 22a is operating within tolerances. The software 200 may indicate that the wand 22a is ready by turning the Wand Ready LED 134c green. The software 200 may also start a timer which will allow the wand 22a to be disconnected and reconnected to the controller for a period to time (e.g., 5 hours) after the fuse is blown.

The controller 20 may determine the adjustments or fine tuning to be made about the center frequencies or channels during Wand Initialization Mode 510. In particular, the controller 20 may determine the particular frequency in each of the frequency bands that elicits the response with the highest voltage. The controller may determine such be varying the capacitance of the LC circuit using the switched capacitors C33-C36 during the Wand Initialization Mode 510. The particular combination of switched capacitors C33-C36 which achieved the response with the highest voltage may then be automatically employed during the Scan Mode 514 (discussed below) to adjust or fine tune about the center frequency or channel in each broad band of transmission. Other approaches to determining the fine tuning may be employed.

If the software 200 does not successfully complete the Wand Initialization Mode 510, the software 200 enters an Invalid Wand Mode 512. If the software 200 successfully completes the Wand Initialization Mode 510, the software 200 progresses to the Scan Mode 514 to automatically start scanning.

In the Invalid Wand Mode 512, the software 200 may blink the Wand Ready LED 134c yellow and issues a slow beep pattern.

The Invalid Wand Mode may be entered in response to any of the following conditions:

- The wand 22a connected to the controller 20 is out of tolerance.
- The controller 20 is unable to blow the fuse in the wand 22a.
- The wand 22a does not have a fuse and more than the set time period has past (e.g., 5 hours) since a fuse was blown.
- The wand 22a does not have a fuse and the controller 20 has been restarted.
- The wand 22a has been connected to the controller for more than the set time period (e.g., 5 hours).
- The wand 22a is detuned due to close proximity to metal.

The corrective action for the Invalid Wand Mode 512 is to remove the invalid wand 22a and attach a new wand 22a to the controller 20 that contains a fuse or to reconnect the wand 22a while holding it in the air at least 2 feet away from large metallic objects.

The software 200 enters the Scan Mode 514 when the wand 22a is ready and the operator presses a Start/Stop button. The software 200 may issue a short three beep pattern via the speaker or beeper 130 when entering the Scan Mode 514 to identify the entry to the user.

In the Scan Mode 514, the software 200 may continuously or periodically perform the following functions.

Look for response signals from transponders 26
Monitor the noise level
Insure the wand 22a is connected and operating correctly
Blink the LED's in a circular pattern When the operator or user pushes the Start/Stop button or the a scan maximum time interval (e.g., 4 minute) has been reached, the software 200 may issue a short three beep pattern and return to the Wand Ready Mode 516.

When an appropriate response signal from a transponder 26 is detected while in Scan Mode 514, the software 200 may turn ON an amber DETECT LEDs 134d and/or provide an audible alarm. The alarm may, for example, beep a continuous solid tone as long as the transponder is detected, with a minimum of beep duration of, for instance 0.5 second.

If the software 200 detects the wand 22a is disconnected while in the Scan Mode 514, the software 200 enters the Scan Fault Mode 520. In the Scan Fault Mode 520, the software 200 may issue a sequence of rapid beeps and blink ON and OFF the amber DETECT LEDs 134d. The Scan Fault Mode 520 can be cleared by pushing the Start/Stop button. The software 200 will automatically clear the scan fault mode 520 after 10 beeps.

While in the Scan Mode 514, if excess noise or loss of transmit signal is detected, the software 200 will progress to the Environment Error Mode 522. In the Environment Error Mode 522, the software 200 may issue or produce an appropriate indication. For example, the software 200 may cause the production of a sequence of slow beeps and the blinking ON and OFF the green circle LEDs 134e. The corrective action for the Environment Error Mode 522 is to reposition the wand 22a away from large metal objects or sources of electrical interference. The software 200 will automatically stop the scan if the environment error condition lasts for more than a set time or number of beeps (e.g., 5 beeps).

Figure 18:
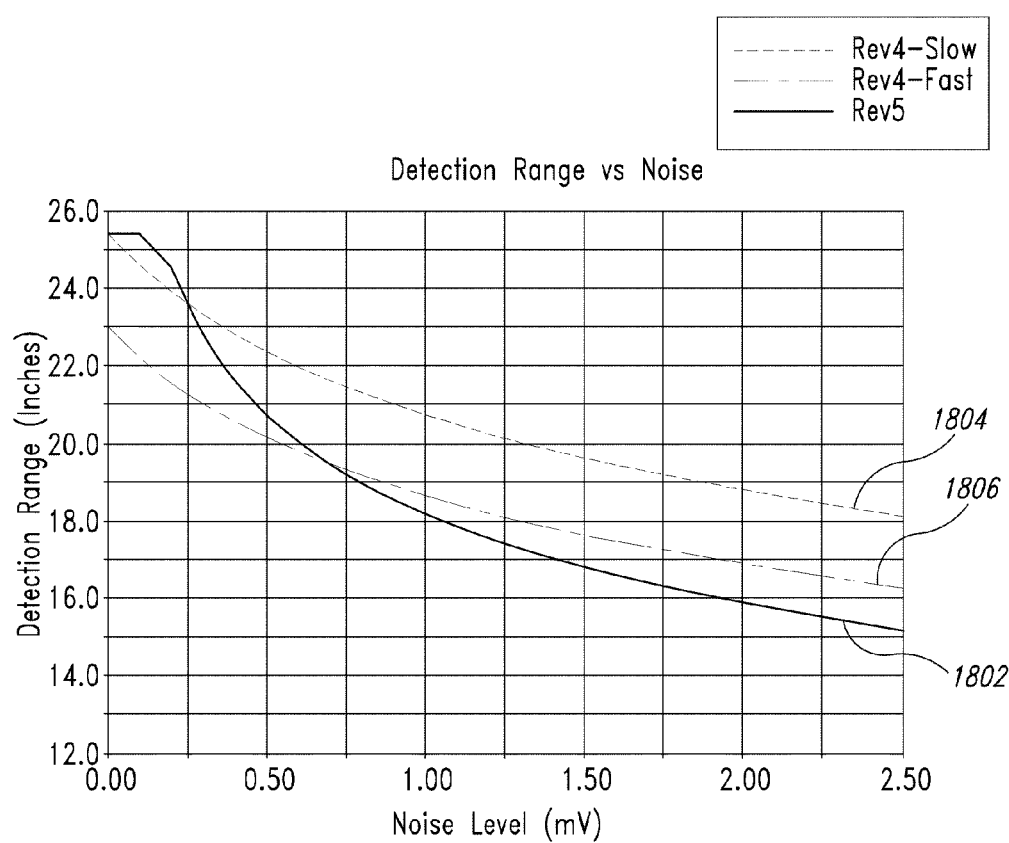
FIG. 18 is a graph showing detection range versus noise achievable by a current embodiment and previous embodiments, for comparison purposes.

FIG. 18 shows a detection range versus noise performance 1802 achievable by the embodiment described herein, as well as the detection range versus noise performance 1804 achievable a "slow" version and the detection range versus noise performance 1806 achievable by a "fast" version of embodiments disclosed in U.S. non-provisional patent application Ser. No. 11/743,104, filed May 1, 2007. As can be appreciated from FIG. 18, the embodiment of the present disclosure is capable of achieving far superior performance, having greater detection range in even mildly noisy environments. Such is particularly advantageous in environments such as operating theaters, and substantially helps reduce false readings (e.g., false positives, false negatives). Thus, such may provide the level of performance demanded by hospitals and doctors.

FIG. 19 shows a method 1900 of operating an interrogation and detection system, according to one illustrated embodiment. The method 1900 may be implemented by any of the interrogation and detection system embodiments discussed above.

During each of a plurality of detection cycles, the interrogation and detection system performs a number of acts 1902-1914. At 1902, the interrogation and detection system receives electromagnetic signals, for example unmodulated electromagnetic signals, during a noise detection portion of the detection cycle. The below descriptions will be presented in terms of unmodulated electromagnetic signals due to the unique technical advantages realized by a system that employs simple resonant transponders without any on-board memory or storage, and from which information cannot be read from or written to. However, some embodiments may employ readable and/or writable transponders, for instance radio frequency identification (RFID) transponders or tags, which respond with a modulated electromagnetic signal that encodes information in the modulation. The various techniques described herein are applicable to such transponders and modulated electromagnetic signals.

At 1904, the interrogation and detection system determines a noise value indicative of a noise level that corresponds to a highest one of a number N of samples or measurements of the unmodulated electromagnetic signals received during the noise detection portion of the detection cycle, where the number N is greater than one. At 1906, the interrogation and detection system adjusts a signal detection threshold based at least in part on the determined noise value of at least one of the detection cycles.

At 1908, a transmitter of the interrogation and detection system emits at least one electromagnetic interrogation signal during a transmit portion of the detection cycle. At 1910, a receiver of the interrogation and detection system receives unmodulated electromagnetic signals during a receive response portion of the detection cycle that follows the transmit portion of the detection cycle.

At 1912, a presence or absence determiner of the interrogation and detection system determines the presence or absence of a transponder based at least in part on a number M of samples or measurements of the unmodulated electromagnetic signals received during the detection cycle and the adjusted signal detection threshold, where the number M is greater than one. A ratio of N:M may be at least equal to 4. N may be equal to about 200 and M may be equal to about 800. The presence or absence determiner may be implemented as part of the controller or as a dedicated circuit, and may be implemented as a hardwired circuit or as a programmed circuit which may include a processor or other programmable element (e.g., FPGA, ASIC).

FIG. 20 shows a method 2000 of operating an interrogation and detection system, according to one illustrated embodiment. The method 2000 may be employed in determining a noise value 1904 of method 1900 (FIG. 19).

At 2002, a noise level determiner of the interrogation and detection system determines a noise value indicative of a noise level based at least in part on the unmodulated electromagnetic signals received during the noise detection portion of the detection cycle by setting the noise value based on the highest one of six samples or measurements of the unmodulated electromagnetic signal received during the noise detection portion of the detection cycle. The noise level determiner may be implemented as part of the controller or as a dedicated circuit, and may be implemented as a hardwired circuit or as a programmed circuit which may include a processor or other programmable element (e.g., FPGA, ASIC).

FIG. 21 shows a method 2100 of operating an interrogation and detection system, according to one illustrated embodiment. The method 2100 may be employed in adjusting the signal detection threshold 1906 of method 1900 (FIG. 19).

At 2102, a detection threshold adjuster of the interrogation and detection system adjusts the signal detection threshold by adjusting the signal detection threshold based at least in part on a first number of determined noise values indicative of a noise level during at least one noise detection portion that occurred before the receive response portion of a first one of the detection cycles and a second number of determined noise values indicative of a noise level during at least one noise detection portion that occurred after the receive response portion of the first one of the detection cycles. The detection threshold adjuster may be implemented as part of the controller or as a dedicated circuit, and may be implemented as a hardwired circuit or as a programmed circuit which may include a processor or other programmable element (e.g., FPGA, ASIC).

FIG. 22 shows a method 2200 of operating an interrogation and detection system, according to one illustrated embodiment. The method 2200 may be employed in adjusting the signal detection threshold 1906 of method 1900 (FIG. 19).

At 2202, a detection threshold adjuster of the interrogation and detection system adjusts the signal detection threshold based at least in part on the determined noise value of at least one of the detection cycles by adjusting the signal detection threshold to be approximately twice an average of at least one of the first and the second number of determined noise values.

FIG. 23 shows a method 2300 of operating an interrogation and detection system, according to one illustrated embodiment. The method 2300 may be employed in adjusting the signal detection threshold 1906 of method 1900 (FIG. 19).

At 2302, a detection threshold adjuster of he interrogation and detection system adjusts the signal detection threshold based at least in part on the determined noise value of at least one of the detection cycles by adjusting the signal detection threshold to be approximately twice a greatest one of at least one of the first and the second number of determined noise values.

FIG. 24 shows a method 2400 of operating an interrogation and detection system, according to one illustrated embodiment. The method 2400 may be employed in determining the presence or absence of a transponder 1912 of method 1900 (FIG. 19).

At 2402, a presence or absence determiner of the interrogation and detection system determines the presence or absence of a transponder by comparing a maximum value of a plurality of matched filter outputs with the adjusted signal threshold.

FIG. 25 shows a method 2500 of operating an interrogation and detection system, according to one illustrated embodiment. The method 2500 may be employed in adjusting the signal detection threshold 1906 of method 1900 (FIG. 19).

At 2502, a detection threshold adjuster of the interrogation and detection system adjusts the signal detection threshold based at least in part on the determined noise value of at least one of the detection cycles by adjusting the signal detection threshold to be approximately twice the determined noise value.

FIG. 26 shows a method 2600 of operating an interrogation and detection system, according to one illustrated embodiment. The method 2600 may be employed in adjusting the signal detection threshold 1906 of method 1900 (FIG. 19).

At 2602, a detection threshold adjuster of the interrogation and detection system adjusts the signal detection threshold based at least in part on the determined noise value of at least one of the detection cycles includes adjusting the signal detection threshold to be the large of approximately twice the determined noise value or a defined threshold value. The defined threshold value may for example be approximately 0.5 mV.

FIG. 27 shows a method 2700 of operating an interrogation and detection system, according to one illustrated embodiment. The method 2700 may be employed to prevent extraneous objects (e.g., metal table, EKG leads, etc.) from producing a positive result.

At 2702, a comparator of the interrogation and detection system determines if an output of at least one matched filter during the noise detection portion of the detection cycle exceeds a noise fault threshold indicative of a noise fault.

FIG. 28 shows a method 2800 of operating an interrogation and detection system, according to one illustrated embodiment. The method 2800 may be employed in performing 2702 of method 2700 (FIG. 27).

At 2802, a comparator or controller of the interrogation and detection system determines if the output of the at least one matched filter during the noise detection portion of the detection cycle exceeds the noise fault threshold for a defined period of time. At 2804, the interrogation and detection system terminates the detection cycle in response to the output of the at least one matched filter exceeding the noise fault threshold for the defined period of time. The comparator may be implemented as part of the controller or as a dedicated circuit, and may be implemented as a hardwired circuit or as a programmed circuit which may include a processor or other programmable element (e.g., FPGA, ASIC).

FIG. 29 shows a method 2900 of operating an interrogation and detection system, according to one illustrated embodiment. The method 2900 may be employed in performing 1908 of method 1900 (FIG. 19).

At 2902, a transmitter of the interrogation and detection system emits at least one electromagnetic interrogation signal during a transmit portion of the detection cycle by emitting at least one electromagnetic interrogation signal in each of a 136 KHz band, a 139 KHz band, a 142 KHz band, a 145 KHz band, a 148 KHz band, a 151 KHz band and a 154 KHz band.

FIG. 30 shows a method 3000 of operating an interrogation and detection system, according to one illustrated embodiment. The method 3000 may be useful in preventing false positives (i.e., tag detections) from being triggered by the transmission of the interrogation or excitement signals.

At 3002, the controller of the interrogation and detection system ignores any unmodulated electromagnetic signals received during a recovery portion of the detection cycle that precedes the receive response portion of the detection cycle.

FIG. 31 shows a method 3100 of operating an interrogation and detection system, according to one illustrated embodiment. The method 3100 may be useful in preventing false positives (i.e., tag detections) from being triggered by energy left in the antenna after the transmission of the interrogation or excitement signals.

At 3102, the controller of the interrogation and detection system dumps energy from an antenna circuit during a dump portion of the detection cycle that precedes the recovery portion of the detection cycle.

FIG. 32 shows a method 3200 of operating an interrogation and detection system, according to one illustrated embodiment. The method 32 may be useful in de-correlating the response signal received from the transponder from constant frequency sources of interference, if any.

At 3202, a ditherer or controller of the interrogation and detection system varies a time between a start of a first one of the successive pairs of the detection cycles and a start of a next successive one of the pairs of the detection cycles. The ditherer may be implemented as part of the controller or as a dedicated circuit, and may be implemented as a hardwired circuit or as a programmed circuit which may include a processor or other programmable element (e.g., FPGA, ASIC).

FIG. 33 shows a method 3300 of operating an interrogation and detection system, according to one illustrated embodiment. The method 3300 may be employed in performing 1908 of the method 1900 (FIG. 19).

The transmitter interrogation and detection system emits at least one electromagnetic interrogation signal during a transmit portion of the detection cycle by at 3302 emitting a first wide band electromagnetic interrogation signal during a first transmit portion of the detection cycle and at 3304 emitting at least a second wide band electromagnetic interrogation signal during a second transmit portion of the detection cycle.

FIG. 34 shows a method 3400 of operating an interrogation and detection system, according to one illustrated embodiment. The method 3400 may be employed in performing 1912 of the method 1900 (FIG. 19), for example in lieu of the match filtering 2400, 2700, 2800 (FIGS. 24, 27 and 28, respectively).

At 3402, a receiver or controller of the interrogation and detection system converts the received signal(s) from the time domain to the frequency domain spectrum. The interrogation and detection system may, for example, perform a Fourier transform, for instance a fast Fourier transform such as a 256 point fast Fourier transform. Suitable algorithms and/or sets of software code for performing such are available or can be written.

At 3404, the receiver or controller of the interrogation and detection system searches the frequency domain spectrum to determine the object with the strongest resonance in a defined frequency band. For example, the interrogation and detection system may search the frequency domain spectrum from about 120 KHz to about 175 KHz. An amplitude of the resonant object may be computed as the sum of the resonant power plus and minus 2 fast Fourier transform bins from the peak resonance frequency. This approach may provide a more accurate measurement of power than simply using the peak value. The frequency of the resonant object may be computed using an interpolation approach. This approach may provide a more accurate determination of resonant frequency than simply using the fast Fourier bin number.

At 3406, a presence or absence determiner of the interrogation and detection system determines the presence or absence of a transponder based at least in part on a frequency of the unmodulated electromagnetic signals received during the detection cycle being within a defined frequency range. The defined frequency range may extend from about 137 KHz to about 160 KHz. The presence or absence determiner may be implemented as part of the controller or as a dedicated circuit, and may be implemented as a hardwired circuit or as a programmed circuit which may include a processor or other programmable element (e.g., FPGA, ASIC).

FIG. 35 shows a method 3500 of operating an interrogation and detection system, according to one illustrated embodiment. The method 3500 may be employed in performing 1912 of the method 1900 (FIG. 19).

At 3502, a presence or absence determiner of the interrogation and detection system determines a Q value (i.e., Quality factor) of the resonant object from a signal decay slope for the received unmodulated electromagnetic signal(s) returned by the resonant object. The interrogation and detection system may, for example, use multiple windows, for instance five (5) window positions may provide suitable results.

At 3504, the presence or absence determiner of the interrogation and detection system determines the presence or absence of a transponder based at least in part on a Q value of the unmodulated electromagnetic signal(s) received during the detection cycle. The interrogation and detection system may preferably employ the Q value determination in conjunction with determination based on the frequency 3402 (FIG. 34) and on the determination based on the adjusted signal detection threshold 1914 (FIG. 19).

FIG. 36 shows a method 3600 of operating an interrogation and detection system, according to one illustrated embodiment. The method 3600 may be employed in performing 1912 of the method 1900 (FIG. 19).

At 3602, a presence or absence determiner the interrogation and detection system determines the presence or absence of a transponder is based at least in part on a Q value of the unmodulated electromagnetic signals received during the detection cycle being at least equal to a threshold Q value. The threshold Q value may be 35. The interrogation and detection system may preferably employ the Q value determination in conjunction with determination based on the frequency 3402 (FIG. 34) and on the determination based on the adjusted signal detection threshold 1914 (FIG. 19). The presence or absence determiner may be implemented as part of the controller or as a dedicated circuit, and may be implemented as a hardwired circuit or as a programmed circuit which may include a processor or other programmable element (e.g., FPGA, ASIC).

Consequently, tag detection may advantageously be based on the received unmodulated electromagnetic signal(s) satisfying all three conditions: 1) measured amplitude is above a threshold, which may be an adjustable threshold, 2) measured frequency is between a lower limit and an upper limit, and 3) measured Q value is above a minimum Q threshold. Interference, for example from RFID tags or EKG cables, are rejected when any of the following three conditions are satisfied: a) measured frequency is below the lower frequency limit, b) measured frequency is above the upper frequency limit, or c) measured Q value is below the threshold Q value. Such may provided significantly superior results over previous approaches, preventing false positives which could otherwise cause a patient to remain open for longer period of time during surgery and tie up hospital personnel and resources.

The above description of illustrated embodiments, particularly the pulsed wide band frequency hopping with dynamic adjustment of the transmission frequency in the various frequency bands and the use of switched capacitors to achieve such, advantageously permit the use of inexpensive transponders which are not accurately tuned to a chosen or selected resonant frequency. This is in marked contrast to the approach typically taken with other types of resonant transponders (i.e., transponders without memory). Such approaches typically interrogate or excite the resonant transponder using narrow frequency bands centered closely on specific frequencies, to achieve a selected resonant response from a highly accurate transponder in order to differentiate signal from noise. This is also in marked contrast to the approach typically taken with radio frequency identification (RFID) tags whether active or passive, which also typically employ are narrow band to achieve a selected response from a highly accurate RFID tag.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other transponders and interrogation and detection systems, not necessarily the exemplary surgical object transponders and interrogation and detection systems generally described above.

For instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms of taught herein are capable of being distributed as a program product in a variety of forms, and that an illustrative embodiment applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

The various embodiments described above can be combined to provide further embodiments. U.S. Provisional patent application Ser. No. 61/056,787, filed May 28, 2008; U.S. Provisional patent application Ser. No. 61/091,667, filed Aug. 25, 2008; U.S. Provisional patent application No. 60/811,376 filed Jun. 6, 2006; U.S. Pat. No. 6,026,818, issued Feb. 22, 2000; U.S. patent Publication No. US 2004/0250819, published Dec. 16, 2004; U.S. provisional patent application Ser. No. 60/811,376, filed Jun. 6, 2006 and U.S. non-provisional patent application Ser. No. 11/743,104, filed May 1, 2007, are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of operation of a transponder detection device, the method comprising:
   during each of a plurality of detection cycles,
   receiving electromagnetic signals by a receiver during a noise detection portion of the detection cycle;
   determining a noise value indicative of a noise level that corresponds to a highest one of a number N of samples or measurements of the electromagnetic signals received during the noise detection portion of the detection cycle by a processor circuit, where the number N is greater than one;
   adjusting a signal detection threshold by the processor circuit based at least in part on the determined noise value of at least one of the detection cycles;
   emitting at least one electromagnetic interrogation signal during a transmit portion of the detection cycle by a transmitter;
   receiving electromagnetic signals by the receiver during a receive response portion of the detection cycle that follows the transmit portion of the detection cycle; and
   determining the presence or absence of a transponder by the processor circuit based at least in part on a number M of samples or measurements of the electromagnetic signals received during the detection cycle and the adjusted signal detection threshold, where the number M is greater than one.

2. The method of claim 1 wherein determining a noise value indicative of a noise level based at least in part on the electromagnetic signals received during the noise detection portion of the detection cycle includes setting the noise value by the processor circuit based on the highest one of six samples or measurements of the electromagnetic signal received during the noise detection portion of the detection cycle.

3. The method of claim 1 wherein adjusting a signal detection threshold by the processor circuit based at least in part on the determined noise value of at least one of the detection cycles includes adjusting the signal detection threshold based at least in part on a first number of determined noise values indicative of a noise level during at least one noise detection portion that occurred before the receive response portion of a first one of the detection cycles and a second number of determined noise values indicative of a noise level during at least one noise detection portion that occurred after the receive response portion of the first one of the detection cycles.

4. The method of claim 3 wherein adjusting a signal detection threshold by the processor circuit based at least in part on the determined noise value of at least one of the detection cycles includes adjusting the signal detection threshold to be approximately twice an average of at least one of the first and the second number of determined noise values.

5. The method of claim 3 wherein adjusting a signal detection threshold by the processor circuit based at least in part on the determined noise value of at least one of the detection cycles includes adjusting the signal detection threshold to be approximately twice a greatest one of at least one of the first and the second number of determined noise values.

6. The method of claim 3 wherein determining the presence or absence of a transponder by the processor circuit includes comparing a maximum value of a plurality of matched filter outputs with the adjusted signal threshold.

7. The method of claim 1 wherein adjusting a signal detection threshold by the processor circuit based at least in part on the determined noise value of at least one of the detection cycles includes adjusting the signal detection threshold to be approximately twice the determined noise value.

8. The method of claim 1 wherein adjusting a signal detection threshold by the processor circuit based at least in part on the determined noise value of at least one of the detection cycles includes adjusting the signal detection threshold to be the large of approximately twice the determined noise value or a defined threshold value.

9. The method of claim 1 wherein the defined threshold value is approximately 0.5 mV.

10. The method of claim 1 wherein a ratio of N:M is at least equal to 4.

11. The method of claim 10 wherein N is equal to about 200 and M is equal to about 800.

12. The method of claim 1, further comprising:
determining if an output of at least one matched filter during the noise detection portion of the detection cycle exceeds a noise fault threshold indicative of a noise fault.

13. The method of claim 12, further comprising:
determining if the output of the at least one matched filter during the noise detection portion of the detection cycle exceeds the noise fault threshold for a defined period of time; and
terminating the detection cycle in response to the output of the at least one matched filter exceeding the noise fault threshold for the defined period of time.

14. The method of claim 12 wherein emitting at least one electromagnetic interrogation signal during a transmit portion of the detection cycle by a transmitter includes emitting at least one electromagnetic interrogation signal in each of a 136 KHz band, a 139 KHz band, a 142 KHz band, a 145 KHz band, a 148 KHz band, a 151 KHz band and a 154 KHz band by the transmitter.

15. The method of claim 1, further comprising:
ignoring any electromagnetic signals received during a recovery portion of the detection cycle that precedes the receive response portion of the detection cycle.

16. The method of claim 1, further comprising:
dumping energy from an antenna circuit during a dump portion of the detection cycle that precedes the recovery portion of the detection cycle.

17. The method of claim 1, further comprising:
for each successive pair of detection cycles, varying a time between a start of a first one of the successive pairs of the detection cycles and a start of a next successive one of the pairs of the detection cycles.

18. The method of claim 1 wherein the transmit and the receive response portions each occur during an interrogation portion of the detection cycle, which follows the noise detection portion of the detection cycle.

19. The method of claim 1 wherein emitting at least one electromagnetic interrogation signal during a transmit portion of the detection cycle by a transmitter includes emitting a first wide band electromagnetic interrogation signal during a first transmit portion of the detection cycle and emitting at least a second wide band electromagnetic interrogation signal during a second transmit portion of the detection cycle.

20. The method of claim 1 wherein determining the presence or absence of a transponder by the processor circuit is based at least in part on a frequency of the electromagnetic signals received during the detection cycle being within a defined frequency range.

21. The method of claim 20 wherein the defined frequency range extends from about 137 KHz to about 160 KHz.

22. The method of claim 1 wherein determining the presence or absence of a transponder by the processor circuit is based at least in part on a Q value of the electromagnetic signals received during the detection cycle.

23. The method of claim 1 wherein determining the presence or absence of a transponder by the processor circuit is based at least in part on a Q value of the electromagnetic signals received during the detection cycle being at least equal to a threshold Q value.

24. The method of claim 23 wherein the threshold Q value is 35.

25. The method of claim 1 wherein receiving electromagnetic signals by a receiver during a receive response portion of the detection cycle that follows the transmit portion of the detection cycle includes receiving unmodulated electromagnetic signals during the receive response portion of the detection cycle.

26. A transponder detection system, comprising:
a transmitter configured to transmit electromagnetic interrogation signals during at least one transmit portion of each of a plurality of detection cycles;
a receiver configured to receive electromagnetic signals during a noise detection portion and a receive response portion of each of the detection cycles; and
a controller communicatively coupled to the transmitter and the receiver and that includes:
a noise level determiner that determines a noise level that corresponds to a highest one of a number N of samples or measurements of the electromagnetic signals received during the noise detection portion of the detection cycles, the noise detection portion temporally spaced from the transmit portions such that transponders are not responding to the electromagnetic interrogation signals;
a detection threshold adjuster that adjusts a detection threshold of the transponder detection system based at least in part on at least one value indicative of at least one of the noise levels; and
a presence or absence determiner that determines a presence or absence of the transponders based at least in part on a number M of samples or measurements of the received electromagnetic signals and the adjusted detection threshold.

27. The transponder detection system of claim 26 wherein noise level determiner is configured to set the noise value based on the highest one of six samples or measurements of the electromagnetic signal received during the noise detection portion of the detection cycle.

28. The transponder detection system of claim 26 wherein the detection threshold adjuster is configured to adjust adjusting the signal detection threshold based at least in part on a first number of determined noise values indicative of a noise level during at least one noise detection portion that occurred before the receive response portion of a first one of the detection cycles and a second number of determined noise values indicative of a noise level during at least one noise detection portion that occurred after the receive response portion of the first one of the detection cycles.

29. The transponder detection system of claim 26, further comprising:
a comparator coupled to determine if the output of the at least one matched filter during the noise detection portion of the detection cycle exceeds the noise fault threshold for a defined period of time; and wherein the controller is configured to terminate the detection cycle in response to the output of the at least one matched filter exceeding the noise fault threshold for the defined period of time.

30. The transponder detection system of claim 26 wherein the controller is configured to ignore any electromagnetic signals received during a recovery portion of the detection cycle that precedes the receive response portion of the detection cycle; to dump energy from an antenna circuit during a dump portion of the detection cycle that precedes the recovery portion of the detection cycle; and to vary a time between a start of a first one of the successive pairs of the detection cycles and a start of a next successive one of the pairs of the detection cycles.

31. The transponder detection system of claim 26 wherein the transmitter includes a frequency adjuster configured to adjust a center frequency of the electromagnetic interrogation signals between successive transmit portions of the detection cycle.

32. The transponder detection system of claim 26 wherein the presence or absence determiner is configured to determine the presence or absence of a transponder is based at least in part on a frequency of the electromagnetic signals received during the detection cycle being within a defined frequency range.

33. The transponder detection system of claim 32 wherein the defined frequency range extends from about 137 KHz to about 160 KHz.

34. The transponder detection system of claim 26 wherein the presence or absence determiner is configured to determine the presence or absence of a transponder based at least in part on a Q value of the electromagnetic signals received during the detection cycle.

35. The transponder detection system of claim 26 wherein the presence or absence determiner is configured to determine the presence or absence of a transponder based at least in part on a Q value of the electromagnetic signals received during the detection cycle being at least equal to a threshold Q value.

36. The transponder detection system of claim 35 wherein the threshold Q value is 35.

37. The transponder detection system of claim 26 wherein the receiver for receiving electromagnetic signals during a noise detection portion includes a receiver that receives unmodulated electromagnetic signals during the noise detection and the receive response portions of each of the detection cycles.

* * * * *